(12) United States Patent
Bugnon et al.

(10) Patent No.: US 9,346,963 B2
(45) Date of Patent: May 24, 2016

(54) SURFACE-MODIFIED PIGMENT PREPARATIONS

(75) Inventors: Philippe Bugnon, Le Mouret (CH); Peter Nesvadba, Marly (CH)

(73) Assignee: BASF SE, Ludwigshafen (DE)

( * ) Notice: Subject to any disclaimer, the term of this patent is extended or adjusted under 35 U.S.C. 154(b) by 264 days.

(21) Appl. No.: 13/976,045

(22) PCT Filed: Dec. 15, 2011

(86) PCT No.: PCT/EP2011/072862
§ 371 (c)(1),
(2), (4) Date: Jun. 26, 2013

(87) PCT Pub. No.: WO2012/089516
PCT Pub. Date: Jul. 5, 2012

(65) Prior Publication Data
US 2013/0289174 A1    Oct. 31, 2013

Related U.S. Application Data

(60) Provisional application No. 61/428,237, filed on Dec. 30, 2010.

(30) Foreign Application Priority Data

Dec. 30, 2010    (EP) ..................... 10197355

(51) Int. Cl.
| | |
|---|---|
| C08K 9/00 | (2006.01) |
| C09D 7/00 | (2006.01) |
| C07C 245/04 | (2006.01) |
| C07C 255/65 | (2006.01) |
| C07C 281/20 | (2006.01) |
| C07C 309/51 | (2006.01) |
| C07F 9/38 | (2006.01) |
| C07F 9/40 | (2006.01) |
| C09B 67/08 | (2006.01) |
| C09B 67/22 | (2006.01) |
| C09B 67/00 | (2006.01) |
| C09D 11/037 | (2014.01) |

(52) U.S. Cl.
CPC ............. *C09D 7/007* (2013.01); *C07C 245/04* (2013.01); *C07C 255/65* (2013.01); *C07C 281/20* (2013.01); *C07C 309/51* (2013.01); *C07F 9/3808* (2013.01); *C07F 9/3882* (2013.01); *C07F 9/4006* (2013.01); *C09B 67/0004* (2013.01); *C09B 67/0034* (2013.01); *C09B 68/26* (2013.01); *C09B 68/4475* (2013.01); *C09D 11/037* (2013.01); *C07C 2101/14* (2013.01); *C07C 2101/20* (2013.01)

(58) Field of Classification Search
CPC ............... C09D 7/007; C09D 11/037
See application file for complete search history.

(56) References Cited

U.S. PATENT DOCUMENTS

| | | | |
|---|---|---|---|
| 3,494,943 A | 2/1970 | Krsek | |
| 5,001,228 A | 3/1991 | Shiraki et al. | |
| 5,718,998 A * | 2/1998 | Takahashi | G03G 5/0696 430/76 |
| 5,837,045 A | 11/1998 | Johnson et al. | |
| 5,851,280 A | 12/1998 | Belmont et al. | |
| 5,907,041 A | 5/1999 | Newsome | |
| 6,090,927 A | 7/2000 | Newsome | |
| 6,398,858 B1 | 6/2002 | Yu et al. | |
| 6,506,245 B1 | 1/2003 | Kinney et al. | |
| 6,896,726 B2 | 5/2005 | Bugnon et al. | |
| 8,753,550 B2 * | 6/2014 | Vairon | C08K 5/0041 106/287.21 |
| 2005/0235874 A1 | 10/2005 | Nakamura et al. | |
| 2008/0308005 A1 | 12/2008 | Deroover | |
| 2008/0308006 A1 | 12/2008 | Deroover | |
| 2009/0048375 A1 | 2/2009 | Deroover | |
| 2009/0130399 A1 * | 5/2009 | Takahashi | C07D 251/52 428/195.1 |
| 2010/0196816 A1 | 8/2010 | Schrader | |

FOREIGN PATENT DOCUMENTS

| | | |
|---|---|---|
| DE | 10 2007 031 354 | 1/2009 |
| EP | 0 906 371 | 3/2002 |
| EP | 1 790 698 | 5/2007 |
| EP | 1 942 156 | 7/2008 |
| FR | 1 433 719 | 1/1966 |
| GB | 12 12 289 | 11/1970 |
| JP | 2-149551 A | 6/1990 |
| JP | 11-323229 A | 11/1999 |
| JP | 2001-187764 A | 7/2001 |
| JP | 2002-226726 A | 8/2002 |
| JP | 2009-132848 A | 6/2009 |

(Continued)

OTHER PUBLICATIONS

Yang, Y. et al., "A facile, green, and tunable method to functionalize carbon nanotubes with water-soluble azo initiators by one-step free radical addition", Applied Surface Science, vol. 256, pp. 3286 to 3292, (2010), XP 002643631.

Fernandez, D. A. et al., "Photophysical and Aggregation Studies of t-Butyl-Substituted Zn Phthalocyanines", Photochemistry and Photobiology, vol. 63, No. 6, pp. 784 to 792, (1996), XP 002643627.

Fernandez, D.A. et al., "Synthesis and photophysical properties of a new cationic water-soluble Zn phthalocyanine", Journal of Photochemistry and Photobiology B:Biology, vol. 41, pp. 227 to 232, (1997), XP 002643628.

(Continued)

*Primary Examiner* — Hannah Pak
(74) *Attorney, Agent, or Firm* — Oblon, McClelland, Maier & Neustadt, L.L.P.

(57) ABSTRACT

A pigment preparation is provided, said preparation comprises an organic pigment comprising a chromophore $Q^1$ and a derivative thereof comprising specific organic substituents via an aliphatic carbon atom in an amount of from 0.1 to 30 mol, based on 100 mol of the organic pigment as well as a process for its preparation and to its use in coloring an organic material such as plastics, coatings or inks.

15 Claims, No Drawings

(56) References Cited

FOREIGN PATENT DOCUMENTS

| JP | 2009-235337 A | 10/2009 |
|---|---|---|
| WO | 02 04564 | 1/2002 |
| WO | 2007 113107 | 10/2007 |
| WO | 2010 146034 | 12/2010 |

OTHER PUBLICATIONS

Levin, Ya. A. et al., "Homolytic Reactions of Organophosphorus Compounds X.* Synthesis, Stability, and Homolysis of (Arlazo)— and [ (Arylazo) Alkyl]—Phosphonates", Journal of General Chemistry USSR, vol. 55, No. 6, pp. 1152 to 1158, (Jun. 1, 1985), XP 009149488.

Troger, J. et al., "Uber die Einwirkung von Diazoniumsalzen auf arylsulfonierte Acetonitrile und Propionitrile", Journal Fuer Praktische Chemie, vol. 101, pp. 157 to 170, (Mar. 1, 1921), XP 009149489.

Petrov, K.A. et al., "Hydroxyamino Phosphonates. IV. Synthesis and Properties of alpha—(Hydroxyamino) Phosphonates", Journal of General Chemistry USSR, Cosnultants Bureau, vol. 49, No. 3, pp. 516 to 521, (Mar. 1, 1979), XP 009149487.

Tamhankar, B.V. et al., "Oxidation of Alkylcyanohydrazines to AZO-BIS Nitriles Using Oxone ®—Potassium Bromide in Aqueous Medium", Synthetic Communications, vol. 32, No. 23, pp. 3643 to 3646, (Jan. 1, 2002), XP 009055526.

Neuman, Jr., R.C. et al., "Neutral and Positively Charged Azonitriles. Decomposition Rates and Efficiencies of Radical Production", J. Org. Chem., vol. 36, No. 26, pp. 4046 to 4050, (1971), XP 002643629, Jan. 11, 2016.

Barbe, W. et al., "Struktur und Spannungsenthalpie tetrasubstituierter Bernsteinsaeuredinitrile", Chem. Ber., vol. 116, pp. 1017 to 1041, (1983), XP 002643630.

Lynch, T.R. et al., "Acyl AlkylDiimides. III. Influence of Structure on Decomposition", Can. J. Chem., vol. 51, pp. 1378 to 1383, (1973), XP 002643632.

Peng, H. et al., "Sidewall Carboxylic Acid Functionalization of Single-Walled Carbon Nanotubes", J. Am. Chem. Soc. vol. 125, No. 49, pp. 15174 to 15182, (2003).

Ying, Y. et al., "Functionalization of Carbon Nanotubes by Free Radicals", Organic Letters, vol. 5, No. 9, pp. 1471 to 1473, (2003).

European Search Report Issued Jun. 29, 2011 in European Patent Application No. 10 19 7355 Filed Dec. 12, 2010.

International Search Report Issued Feb. 2, 2012 in PCT/EP11/72862 Filed Dec. 15, 2011.

Office Action dated Feb. 22, 2016 issued in corresponding Japanese patent application No. 2013-546652.

\* cited by examiner

SURFACE-MODIFIED PIGMENT PREPARATIONS

The invention relates to a pigment preparation comprising an organic pigment usually prone to unsatisfactory dispersibility and/or rheology at high concentration, and a derivative thereof comprising one or more specific organic substituents attached via an aliphatic carbon atom, i.e., non-aromatic carbon atom, to a process for their preparation and to its use in pigmenting an organic material such as coatings, plastics and inks.

Many applications require modifying the pigment surface in order to enhance their performance, e.g., dispersibility, dispersion stability and compatibility, which allow a better processing of insoluble pigments. A variety of techniques have been developed, for example, adsorption of a polymer, resination, adsorption of a pigment derivative, treatment with inorganic compounds and, recently, grafting of a specific reactant onto the pigment.

U.S. Pat. No. 6,398,858 discloses a process for preparing colored pigments, using diazotable compounds, and leading to pigments substituted by groups comprising at least one aromatic and/or $C_1$-$C_{20}$alkyl group and at least one ionic, ionizable and/or non-ionic group. The non-ionic groups may include hydrophilic groups, hydrophobic groups, alkyl and aryl groups, ethers, polyethers, alkyls, fluorinated alkyls and the like. The examples use only sulfanilic acid or p-aminobenzoic acid.

U.S. Pat. No. 6,494,943 and U.S. Pat. No. 6,506,245 disclose ink jet inks and other compositions containing colored pigments, wherein the pigments are surface-modified by hydrodynamic cavitation in the presence of a diazotating agent. Surface modification is obtained by linking aromatic groups including aryl and heteroaryl groups, for example, imidazolyl and indolyl. Specific reagents exemplified for surface modifications are sulfanilic acid, p-amino-benzoic acid, N-p-amino-phenyl pyridinium chloride, 3,5-bis(trifluoromethyl)aniline and C. I. Direct Blue 71.

WO 02/04 564 mentions inorganic and organic pigments substituted by at least one organic group of the formula -X-Sp-Alk, wherein X may be arylene, heteroarylene or alkylene, Sp is a spacer, e.g., succinimidylene, and Alk is a long-chain alkyl or alkenyl. Only examples of aryl-substituted carbon black are disclosed.

U.S. Pat. No. 6,896,726 discloses surface-treated organic pigments partially substituted with phenyl or naphthyl groups which are further substituted with linear dispersant groups, for example, C. I. Pigment Red 255 substituted with diazotated procaine or C. I. Pigment Blue 15:3 substituted with diazotated 4-hexadecyl-sulfonylaniline.

EP-A-1790698 discloses a non-aqueous diketopyrrolopyrrole (DPP) pigment dispersion using a DPP derivative containing at least one carboxylic groups attached via a $CH_2$ linking group to a nitrogen atom of the diketopyrrolopyrrole moiety.

US-A-2005/0235874 discloses an image-recording, hydrophilic colorant comprising inter alia a trimellit(monoamido)methyl or 4',6'-bis(dicarboxymethylamino)-s-triazinylaminomethyl derivative of an organic pigment.

DE-A-102007031354 discloses a pigment preparation based on dioxazine comprising a imidazolyl-substituted pigment derivative.

WO 2010/146034 discloses surface-modified pigment compositions by diazotation of anilines annellated with heterocycles having improved rheology properties, especially in high-solids systems.

There is a continuing need for surface-modified pigment preparations. Therefore, it is the object of the present invention to provide a surface-modified pigment preparation having improved rheological and dispersing properties, especially in high-solids coating systems, and/or exhibit no warping in pigmenting of partially crystalline plastics, wherein the coloristic properties of the pigments should not be appreciably influenced by said modification of the pigment surface.

Recently, it has been shown that functionalized multi-walled carbon nanotubes can be obtained by one-step free radical addition of water-soluble azo inititators (Y. Yang et al., Appl. Surface Science 256, 2010, 3286). Attached carboxylic groups may be used as scaffolds to chelate $Ag^+$ ions affording Ag/nanotubes nanohybrides in the presence of a reductant.

A similar method of functionalization of carbon nanotubes by adding free radicals employs alkyl radicals generated by decomposing diacyl peroxides (V. N. Khabashesku et al., J. Am. Chem. Soc. 125, 2003, 15175) or dibenzoyl peroxide in the presence of alkyl iodides or by reacting dialkylsulfoxides with hydrogen peroxide and $Fe^{2+}$ ions (W. E. Billups et al., Org. Lett. 5(9), 2003, 1471).

It has now been found that a pigment preparation with the desired properties is obtained by covalently attaching an organic group to the chromophore of the pigment surface via grafting free radicals, wherein the coloristic properties of the pigments are not be appreciably influenced by the modification of the pigment surface.

Accordingly, in a first aspect the invention relates to a pigment preparation comprising
(a) an organic pigment comprising a chromophore $Q^1$; and
(b) from 0.1 to 30 mol, based on 100 mol of organic pigment (a), of a compound of formula

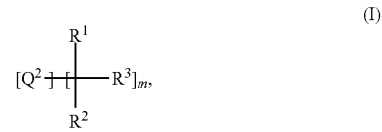

wherein $Q^2$ is a m-valent residue of chromophore $Q^1$;
$R^1$ and $R^2$ are independently of each other CN, $C_1$-$C_6$alkyl, $C_3$-$C_7$cycloalkyl, said alkyl or cycloalkyl is unsubstituted or substituted with D, $C_6$-$C_{18}$aryl, said aryl is unsubstituted or substituted with E; or
$R^1$ and $R^2$ together with the linking carbon atom form a 5 to 12 membered ring, said ring is unsubstituted or substituted with E and said ring may further contain one or more groups selected from —O—, —$NR^4$—, —N(—$OR^4$)—, or —$N^+R^4R^5$ $An^-$—;
$R^3$ is $C_1$-$C_{25}$alkyl, $C_3$-$C_{25}$alkenyl, said alkyl or alkenyl is unsubstituted or substituted with D, $C_7$-$C_{25}$aralkyl, said aryl in $C_7$-$C_{18}$aralkyl is unsubstituted or substituted with E, or a group of formula

p and q are independently of each other 0 or 1;
X is —O—, —S—, —$NR^6$—, —$CONR^6$—, —COO—, or —C(=$NR^7$)$NR^8$—;
Y is $C_1$-$C_{25}$alkylene, said alkylene may contain at the end or within the chain one or more groups selected from —O—, —S—, —CO—, —COO—, —$CONR^6$—, —$NR^6$—, —N⁺R⁶R⁵ An⁻, an alicyclic or aromatic ring, and said alkylene may be substituted one or more times with Z;

Z is H; OR⁹; OCOR⁹; CN; NR⁹R¹⁰; N⁺R⁹R¹⁰R⁵ An⁻; $C_6$-$C_{18}$aryl, said aryl is unsubstituted or substituted with E; COOR⁹; CONR⁹R¹⁰;

$SO_2R^9$; $SO_3R^9$; $SO_2NR^9R^{10}$; $SO_3^-Cat^+$; or $PO(OR^9)_2$; or a heterocyclic $C_2$-$C_{20}$ring system, said ring system contains one or more groups selected from O, S, N, NR⁴, NOR⁴, N⁺R⁴R⁵ An⁻ or N⁺R⁵ An⁻, and said ring system is unsubstituted or substituted with E;

R⁴ is H or $C_1$-$C_4$alkyl, said alkyl is unsubstituted or substituted with D;

R⁵ is H, $C_1$-$C_4$alkyl, $C_7$-$C_{10}$aralkyl or $C_3$-$C_5$alkenyl;

R⁶, R⁷, R⁸, R⁹, R¹⁰, R¹¹, R¹² and R¹³ are independently of each other and in each occurrence H, $C_1$-$C_{18}$alkyl, $C_3$-$C_{18}$alkenyl, $C_5$-$C_{12}$cycloalkyl, said alkyl, alkenyl or cycloalkyl is unsubstituted or substituted with D; $C_6$-$C_{18}$aryl, $C_7$-$C_{18}$aralkyl, said aryl in $C_6$-$C_{18}$aryl or $C_7$-$C_{18}$aralkyl is unsubstituted or substituted with E; or R⁹ and R¹⁰ together with the linking nitrogen atom form a 5 to 7 membered heterocyclic ring, said ring is unsubstituted or substituted with E, and said ring may further contain one or more groups selected from —O—, —NR⁴— or —N⁺R⁴R⁵ An⁻-; or R¹² and R¹³ together with the linking nitrogen atom form a 5 to 7 membered heterocyclic ring, said ring is unsubstituted or substituted with E, and said ring may further contain one or more groups selected from O, N, NR⁴, N⁺R⁴R⁵ An⁻ or N⁺R⁵ An⁻; or R¹¹ and R¹² together with the linking NCN group form a 5 to 7 membered cyclic amidine, said amidine is unsubstituted or substituted with E;

E is $C_1$-$C_4$alkyl, $C_1$-$C_4$alkoxy, COOH, OH, halogen, NR⁹R¹⁰, —N⁺R⁹R¹⁰R⁵ An⁻, $SO_3R^9$, $SO_2NR^9R^{10}$ or $SO_3^-$Cat⁺;

D is $C_1$-$C_4$alkoxy, OH, COOH, or halogen;

An⁻ is an equivalent of a suitable anion;

Cat⁺ is an equivalent of a suitable cation;

m is an integer from 1 to 4; and each group of formula

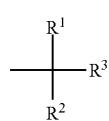

(III)

is selected independently of the others.

The organic pigment (a) comprising a chromophore Q¹ is typically an organic pigment comprising a chromophore Q¹ which comprises at least one group of formula

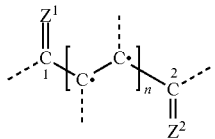

(X)

or a cis/trans isomer thereof, wherein Z¹ and Z² are independently of each other O or N—, each C• is independently of all other C• a carbon atom with an electron in a p orbital, and n is an integer from 1 to 4.

Preferred is a pigment preparation, wherein m is 1 or 2, more preferably m is 1.

Organic pigments comprising conjugated keto or azomethine groups generally lead to poorly satisfactory dispersibility and/or rheology at high concentration, in particular in so-called "high-solids" coatings. This is especially true for organic pigments which are based on point-symmetrical and/or mirror-symmetrical chromophores. For the purpose of the invention, the symmetry of the chromophores should be considered under exclusion of any monovalent peripheral substituents having no or only little influence on the color, such as halogen, alkyl and/or alkoxy. Typical examples of such technically demanding organic pigments are anthanthrone, 1,1'-dianthraquinolyl, bis(anthraquinone-1-yl-amino), bis(anthraquinone-1-yl-oxy), BONA disazo condensation, BONA monoazo (including some benzimidazolone pigments), diketopyrrolopyrrole, dioxazine, flavanthrone, indanthrone, isoindoline, isoindolinone, isoviolanthrone, naphthalocyanine, perylene, phthalocyanine, pyranthrone and quinacridone pigments. Many of said pigments have point-symmetrical chromophores and the [na]phthalocyanines have mirror-symmetrical chromophores, but a few special non-symmetrical pigments from further pigment classes also take advantage of the invention.

Suitable organic pigments are chromophores comprising at least one group of formula

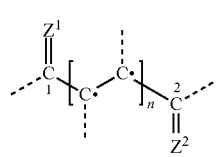

(X)

or a cis/trans isomer thereof, wherein Z¹ and Z² are each independently of each other O or N—, each C• is independently of all others C• a carbon atom with an electron in a p orbital, and n is an integer from 1 to 4, preferably 1 or 2, most preferably 1. The numbers on both oxo/imide-substituted C atoms (C¹, C²) only have the meaning to differentiate them. All C•, C¹, C², Z¹ and Z² are preferably essentially in the same plane (that is, a plane can be drawn which cuts all imaginary covalent spheres around these atoms' kernels, the diameter of which is $1.5 \cdot 10^{-10}$ m {=1.5 Å}, preferably $1 \cdot 10^{-10}$ m {=1 Å}), and they are most preferably part of an extended aromatic or heteroaromatic system. A carbon atom with an electron in a p orbital (C•) is meant to be bonded to 3 atoms (2 simple and 1 double bonds), with its covalent sphere (as defined above) cutting an imaginary plane extending through the kernels of the 3 atoms to which it is bonded. Cis/trans isomers of formula (X) should be understood as formulae resulting from 180° rotations around one or more of the bonds between

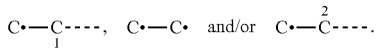

Thus, for example, each

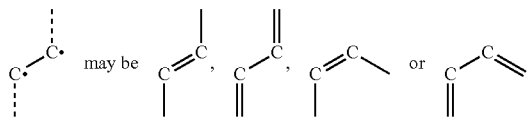

(when n≥2, for each C•-C• independently of the others).

In formula (X), the dashed lines indicate bonds to other atoms of the chromophore, thereby preferably forming aromatic or unsaturated cycles. There may optionally be additional, similar or different links between $C^1$ and $C^2$ in the instant pigments' chromophores (this is, in particular, the case in polycyclic pigments), but this is not necessary as long as there is at least one preferably planar group of the formula (X) wherein n=1-4 for the shortest possible path. However, additional aromatic or unsaturated links do not require all atoms to be in the same plane, and n may also be >4, depending on which path is chosen between $C^1$ and $C^2$.

Compound (b) is in general a derivative of organic pigment (a).

Residues $Q^2$ of the chromophore $Q^1$ are chromophores $Q^1$ from which m peripheral H atoms have been abstracted, thus enabling formation of bonds to m substituents (that is, $Q^1$ is identical with

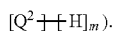

Peripheral H atoms are preferably situated on aromatic C atoms. The chromophore $Q^1$ and the residue $Q^2$ may optionally be substituted by one or more same or different, monovalent peripheral substituents having no major influence on the color, such as halogen, alkyl and/or alkoxy. NH, N-M-N and $NH_2$ groups as well as other substituents having a major influence on the color (that is, substituents shifting the main absorption peak in the range 400-700 nm by ≥50 nm, preferably ≥30 nm, as compared with hydrogen) should be considered to be part of the chromophore $Q^1$ and residue $Q^2$, respectively. When the chromophore $Q^1$ is substituted, its residue $Q^2$ is most adequately identically substituted unless the pigment is a solid solution, in which latter case the chromophore $Q^1$ and the residue $Q^2$ might originate from chemically different molecules of the solid solution (the more reactive ones leading to the substituted residue $Q^2$ and the less reactive ones leading to the remaining unsubstituted chromophore $Q^1$).

Pigment (a) can in principle be any desired organic pigment, provided its surface can be modified by the process according to the invention. Usually, the pigment is a pigment of the anthanthrone, bis(anthraquinone-1-yl-amino), bis(anthraquinone-1-yl-oxy), 1,1'-dianthraquinolyl, anthrapyrimidine, quinacridone, quinacridonequinone, quinophthalone, diketopyrrolopyrrole, dioxazine, flavanthrone, indanthrone, indigo, isoindoline, isoindolinone, isoviolanthrone, perinone, perylene, phthalocyanine, pyranthrone or thioindigo series.

The term "pigment" is to be understood as including also mixtures of the above-mentioned pigments and mixtures of the above-mentioned pigments with other pigments, including solid solutions and mixed crystals, the mixtures consisting customarily of from 2 to 5, preferably 2 or 3, components. Solid solutions and mixed crystals of quinacridones are described, for example, in U.S. Pat. No. 3,160,510. Examples include C.I. (Color Index) Pigment Red 202, 207, 209 and 206 and C.I. Pigment Orange 48 and 49. Solid solutions and mixed crystals of diketopyrrolo[3,4-c]pyrroles (DPP) are described, for example, in U.S. Pat. No. 4,783,540, U.S. Pat. No. 5,529,623, U.S. Pat. No. 5,708,188 and U.S. Pat. No. 6,036,766. Solid solutions and mixed crystals of DPP-type pigments and non-DPP-type pigments, for example, quinacridone or quinacridonequinone, are described in U.S. Pat. No. 4,810,304, U.S. Pat. No. 5,472,496, U.S. Pat. No. 4,810,304 and U.S. Pat. No. 5,821,373. An example is a mixed phase of C.I. Pigment Red 254 and C.I. Pigment Violet 254 (γ-modification). Monophase solid solutions that contain asymmetric pyrrolo[3,4-c]pyrroles as host are described in U.S. Pat. No. 5,756,746. Preference is given to solid solutions and mixed crystals of C.I. Pigment Red 264 or C.I. Pigment Red 255.

The term "grafting" used herein means covalently attaching an organic group to a chromophore of a pigment onto a pigment surface to effect functionalization thereof.

Preferably, the organic group is covalently attached to a carbon atom of a chromophore, in particular to an aromatic carbon atom of a chromophore.

In addition to the group of formula (X), the chromophores of the instant pigments preferably comprise one or more NH, N-M-N or $NH_2$ groups, wherein M is a divalent metal, oxometal or halogeno-metal, such as Cu, Ni, Zn, Al—Cl, Ti=O or V=O.

Preferred chromophores comprising NH, N-M-N or $NH_2$ groups are such of bis(anthraquinone-1-yl-amino), bis(anthraquinone-1-yl-oxy), 1,1'-dianthraquinolyl, diketopyrrolopyrrole, indanthrone, isoindoline, isoindolinone, perylene, 1-phenylhydrazono-2-oxy-3-carbamoyl-1,2-dihydronaphthalene, phthalocyanine and quinacridone pigments. Most preferred are chromophores of 1,1'-dianthraquinolyl, diketopyrrolopyrrole, indanthrone, isoindoline, isoindolinone, perylene, phthalocyanine and quinacridone pigments.

Suitable pigments include, for example, C.I. Pigment Yellow 24, 99, 108, 109, 110, 123, 138, 139, 147, 173, 175, 177, 179, 182, 185, 193, 199 and 257; C.I. Pigment Orange 22, 24, 31, 32, 38, 40, 43, 48, 49, 51, 61, 66, 69, 71, 73 and 81; C.I. Pigment Red 2, 5, 7, 8, 9, 10, 11, 12, 13, 14, 15, 16, 17, 18, 21, 22, 23, 31, 32, 83:1, 88, 90, 95, 112, 114, 119, 122, 123, 136, 144, 146, 147, 148, 149, 150, 164, 166, 168, 170, 174, 175, 176, 177, 178, 179, 180, 181, 184, 185, 187, 188, 190, 192, 194, 202, 204, 206, 207, 208, 209, 210, 212, 213, 214, 216, 220, 221, 222, 223, 224, 226, 238, 242, 245, 248, 253, 254, 255, 256, 258, 260, 261, 262, 264, 270 and 272; C.I. Pigment Brown 1, 23, 25, 38, 41 and 42; C.I. Pigment Violet 5:1, 13, 19, 23, 25, 29, 31, 32, 37, 42, 44 and 50; C.I. Pigment Blue 15, 15:1, 15:2, 15:3, 15:4, 15:6, 16, 25, 26, 60, 63, 64 and 66; C.I. Pigment Green 8, 12, 37, 47, 54 and 58; C.I. Pigment Black 6, 20, 21, 31 and 32; Vat Red 41 and 74; 3,6-di(3',4'-dichlorophenyl)-2,5-dihydro-pyrrolo[3,4-c]pyrrole-1,4-dione, 3,6-di(4'-cyano-phenyl)-2,5-dihydro-pyrrolo[3,4-c]pyrrole-1,4-dione, bisbenzimidazo[2,1-a:2',1'-a']anthra[2,1,9-def:6,5,10-d'e'f]diisoquinoline-10,21-dione [CAS 55034-79-2], anthra-[2",1",9":4,5,6;6",5",10":4',5',6']diisoquino[2,1-a:2',1'-a']diperimidine-12,25-dione [CAS 6859-32-1] and the compounds according to example 12b of WO 00/24736 or obtainable according to the process of WO 2010/081625 (in particular those according to claim 10, 11 or 12 of WO 2010/08125, which are incorporated herein by reference); as well as mixtures, mixed crystals and solid solutions comprising any components of the same chemical formulae and optionally having the same crystal lattice.

Accordingly, in a preferred aspect the invention relates to a pigment preparation, wherein the organic pigment comprising a chromophore $Q^1$ is a pigment selected from bis(anthraquinone-1-yl-amino), bis(anthraquinone-1-yl-oxy), 1,1'-dianthraquinolyl, diketopyrrolopyrrole, indanthrone, isoindoline, isoindolinone, perylene, 1-phenylhydrazono-2-oxy-3-carbamoyl-1,2-dihydronaphthalene, phthalocyanine, quinacridone pigments, or a mixture of said pigments, including a solid solution or a mixed crystal.

In addition to above pigments, the inventive preparations may comprise derivatives of said pigments, which derivatives have the same chromophore as the pigments. These derivatives may conveniently be prepared by partially reacting a pigment with adequate reagents, thus preferably forming pigments on which surface a continuous or discontinuous layer or spots of the derivative is present.

Alkyl, e.g., $C_1$-$C_4$alkyl, $C_1$-$C_6$alkyl, $C_1$-$C_{18}$alkyl, $C_6$-$C_{18}$alkyl or $C_1$-$C_{25}$alkyl, may be within the given limits of carbon atoms linear or branched, where possible. Examples are methyl, ethyl, n-propyl, isopropyl, n-butyl, s-butyl, isobutyl, t-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 2-ethylhexyl, n-nonyl, decyl, undecyl, dodecyl, tridecyl, tetradecyl, pentadecyl, hexadecyl, heptadecyl, octadecyl, eicosyl, heneicosyl, docosyl, tetracosyl and pentacosyl. Alkoxy, e.g., $C_1$-$C_4$alkoxy is alkyl-O—. Each alkyl may be unsubstituted or substituted one or more times with D, as defined above.

Alkylene, e.g., $C_1$-$C_{25}$alkylene, or $C_1$-$C_{18}$alkylene, preferably $C_1$-$C_4$alkylene, $C_1$-$C_6$alkylene or $C_6$-$C_{18}$alkylene, may be derived from above-defined alkyl by abstracting a hydrogen atom from any terminal carbon atom of the alkyl. Examples are methylene, ethylene, n-, isopropylene, n-, iso-, s-, t-butylene, n-pentylene, n-hexylene, n-heptylene, n-octylene, n-nonylene, n-decylene, n-undecylene, n-dodecylene, n-tridecylene, n-tetradecylene, n-pentadecylene, n-hexydecylene, n-heptydecylene, n-octadecylene, eicosylene, heneicosylene, docosylene, tetracosylene and pentacosylene.

Where the alkylene group contains one or more groups selected from —O—, —S—, —CO—, —COO—, —CONR$^6$—, —NR$^6$—, —N$^+$R$^6$R$^5$ An$^-$, an alicyclic or aromatic ring, these groups may be independently present at one or both of the ends and/or within the chain. The groups —COO— and —CONR$^6$— may also be connected as —OCO— and —NR$^6$CO—. Preferably, one, two or three groups are contained, more preferred are one or two groups. Two of said groups may also be directly linked. R$^6$ may be preferably $C_1$-$C_{18}$alkyl, $C_3$-$C_5$alkenyl, $C_5$-$C_7$cycloalkyl, said alkyl, alkenyl or cycloalkyl is unsubstituted or substituted one or more times with D; $C_6$-$C_{12}$aryl, $C_7$-$C_{10}$aralkyl, said aryl in $C_6$-$C_{18}$aryl or $C_7$-$C_{18}$aralkyl is unsubstituted or substituted one or more times with E. The alicyclic group present in the alkylene group may be $C_5$-$C_7$cycloalkylene, for example, cyclopentylene, cyclohexylene, or cycloheptylene, preferably 1,4- or 1,3-cyclohexylene. The aromatic group present in the alkylene group may be phenylene or naphthylene, e.g., o-phenylene, m-phenylene, p-phenylene, 1,4-naphthylene, 1,5-naphthylene or 2,6-naphthylene, preferably p-phenylene. Further, said alkylene may be substituted one or more times with Z, as defined above, preferably 1, 2 or 3 times, especially once.

Alkenyl, e.g., $C_3$-$C_{25}$alkenyl, $C_3$-$C_{18}$alkenyl or $C_3$-$C_5$alkenyl, may be within the given limits of carbon atoms straight-chain or branched, where possible. Examples are allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, oleyl, or n-octadec-4-enyl. The term "alkenyl" also comprises residues with more than one double bond that may be conjugated or non-conjugated, for example, may comprise one double bond. Each alkenyl may be unsubstituted or substituted one or more times with D.

Cycloalkyl, e.g., $C_3$-$C_7$cycloalkyl, $C_5$-$C_{12}$cycloalkyl, or $C_5$-$C_7$cycloalkyl, may be within the given limits of carbon atoms cyclopropyl, cyclobutyl, cyclopentyl, cyclohexyl, cycloheptyl, cyclooctyl, cyclodecyl, cycloundecyl, cyclododecyl, methylcyclopentyl, di methylcyclopentyl, methylcyclohexyl, and dimethylcyclohexyl, preferably cyclohexyl. Each cycloalkyl may be unsubstituted or substituted one or more times with D.

Aryl, e.g., $C_6$-$C_{12}$aryl or $C_6$-$C_{12}$aryl, may be within the given limits of carbon atoms phenyl, fluorenyl, indenyl, azulenyl, naphthyl, biphenylyl, terphenylyl, as-indacenyl, s-indacenyl, acenaphthylenyl, phenanthryl, fluoranthenyl, triphenylenyl, chrysenyl, naphthacenyl, picenyl, perylenyl, pentaphenyl, hexacenyl, pyrenyl, or anthracenyl, preferably phenyl, 1-naphthyl, 2-naphthyl, 9-phenanthryl, 2- or 9-fluorenyl, 3- or 4-biphenylyl, preferably the above-mentioned mono- or bicyclic radicals. Each aryl may be unsubstituted or substituted one or more times with E.

Aralkyl, e.g., $C_7$-$C_{25}$aralkyl, $C_7$-$C_{10}$aralkyl, or $C_7$-$C_{10}$aralkyl may be within the given limits of carbon atoms benzyl, 2-benzyl-2-propyl, β-phenyl-ethyl(phenethyl), α,α-dimethylbenzyl, ω-phenylbutyl, ω,ω-dimethyl-ω-phenyl-butyl, ω-phenyl-dodecyl, ω-phenyl-octadecyl, in which both the aliphatic and the aromatic hydrocarbon group may be unsubstituted or substituted. The aromatic part may be substituted one or more times with E; the aliphatic part may be substituted with D. Preferred examples are benzyl, phenethyl, α,α-dimethylbenzyl, ω-phenyl-butyl, ω-phenyl-dodecyl and ω-phenyl-octadecyl.

Examples of the 5 to 12 membered ring, preferably a saturated ring, formed by, for example, $R^1$ and $R^2$ together with the linking C atom, are cyclopentyl, cyclohexyl, cycloheptyl, cyclooctyl, cyclononyl, cyclodecyl, cycloundecyl and cyclododecyl. Said rings may be unsubstituted or substituted one or more times, preferably 1 to 4 times, with E, and further, said rings may contain one or more moieties of —O—, —NR$^4$—, —N(—OR$^4$)—, or —N$^+$R$^4$R$^5$ An$^-$, preferably one —NR$^4$— or —N(—OR$^4$)—.

Suitable examples of said ring are

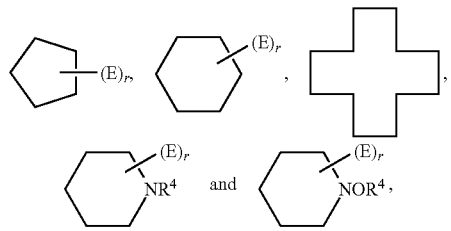

wherein E is independently of each other methyl or ethyl, r is 0, 1, 2, 3 or 4 and R$^4$ is H, methyl, ethyl, propyl, or butyl, for example, a ring of formula

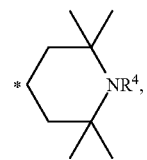

wherein $R^4$ is H or $C_1$-$C_4$alkyl, or of formula

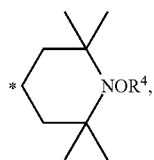

wherein $R^4$ is $C_1$-$C_4$alkyl, and the asterix * denotes the carbon atom which is linked to $R^3$ and $Q^2$ according to formula (I).

Examples of the 5 to 7 membered heterocyclic ring, formed by $R^9$ and $R^{10}$ together with the linking N atom, may be derived from a saturated heterocyclic ring, such as imidazolidine, pyrrolidine, pyrazolidine, piperidine, piperazine, morpholine, azepane, etc. Said ring may be unsubstituted or substituted one or more times with E.

Suitable examples of saturated heterocyclic rings are

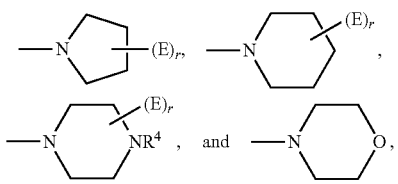

wherein E is independently of each other methyl or ethyl, r is 0, 1, 2, 3 or 4 and $R^4$ is H, methyl, ethyl, propyl or butyl.

Examples of the 5 to 7 membered heterocyclic ring, formed by $R^{12}$ and $R^{13}$ together with the linking N atom may be derived from a saturated heterocyclic ring, such as imidazolidine, pyrrolidine, pyrazolidine, piperidine, piperazine, morpholine, azepane, etc., or from an unsaturated heterocyclic ring, such as pyrrol, pyrroline, imidazole, imidazoline, pyrazole, pyrazoline, triazole, etc. Among them, saturated rings are preferred, wherein the ring may further contain —O— or —$NR^4$— and is unsubstituted or substituted one or more times with E. Where Z is a saturated or unsaturated heterocyclic $C_2$-$C_{20}$ring system, said ring system, which may be mono- or polycyclic, contains one or more groups selected from O, S, N, $NR^4$, $NOR^4$, $N^+R^4R^5$ An⁻ or $N^+R^5$ An⁻, and may be unsubstituted or substituted one or more times with E. Preferably, the $C_2$-$C_{20}$ring system comprises 1 to 4 annellated rings and up to 5 groups selected from O, S, N, $NR^4$, $NOR^4$, $N^+R^4R^5$ An⁻ or $N^+R^5$ An⁻. More preferred, the $C_2$-$C_{20}$ring system comprises 1 to 3, for example 1 or 2, annellated rings and 1 to 3, for example 1 or 2, groups.

Especially, Z is a saturated $C_2$-$C_{20}$ring system or $C_2$-$C_{18}$heteroaryl ring system.

The ring system Z may be $C_2$-$C_{18}$heteroaryl, typically containing groups selected from O, S, N, or $N^+R^5$ An⁻, and which is typically an unsaturated heterocyclic radical with five to 18 atoms having at least six conjugated π-electrons such as thienyl, benzo[b]thienyl, dibenzo[b,d]thienyl, thianthrenyl, furyl, furfuryl, 2H-pyranyl, benzofuranyl, isobenzofuranyl, 2H-chromenyl, xanthenyl, dibenzofuranyl, phenoxythienyl, pyrrolyl, imidazolyl, pyrazolyl, pyridyl, bipyridyl, triazinyl, pyrimidinyl, pyrazinyl, 1H-pyrrolizinyl, isoindolyl, pyridazinyl, indolizinyl, isoindolyl, indolyl, 3H-indolyl, phthalazinyl, naphthyridinyl, quinoxalinyl, quinazolinyl, cinnolinyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, 4aH-carbazolyl, carbolinyl, benzotriazolyl, benzoxazolyl, phenanthridinyl, acridinyl, perimidinyl, phenanthrolinyl, phenazinyl, isothiazolyl, phenothiazinyl, isoxazolyl, furazanyl or phenoxazinyl. Each heteroaryl may be unsubstituted or substituted one or more times with E.

The ring system Z may also be a saturated heterocyclic $C_2$-$C_{20}$ring system, preferably a mono- or bicyclic ring system containing groups selected from O, S, $NR^4$, $NOR^4$, or $N^+R^4R^5$ An⁻, more preferably a mono- or bicyclic system containing —$NR^4$— or —$N(OR^4)$—, for example,

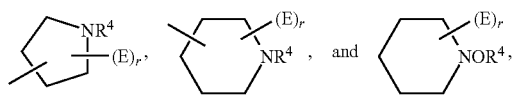

wherein E is independently of each other methyl or ethyl, r is 0, 1, 2, 3 or 4, and $R^4$ is H, methyl, ethyl, propyl, or butyl, for example, a ring of formula

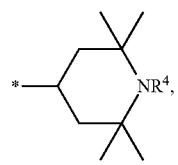

wherein $R^4$ is H or $C_1$-$C_4$alkyl, or of formula

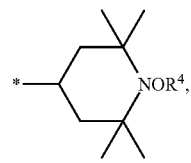

wherein $R^4$ is $C_1$-$C_4$alkyl and the asterix * denotes the linking carbon atom.

Each nitrogen atom within a heterocyclic ring, as defined above for Z, may also be in quaternary form, where possible, in connection with a suitable counter anion. Examples of a heteroaromatic group containing a quaternary nitrogen are

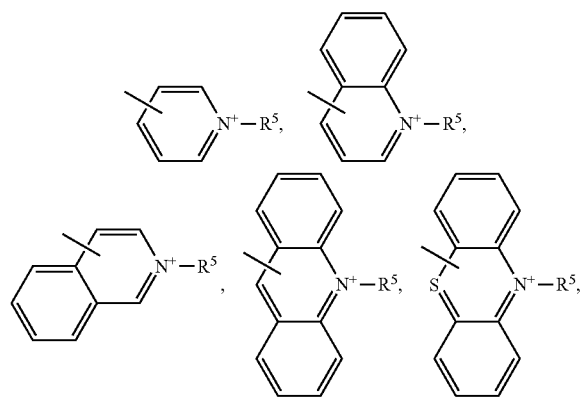

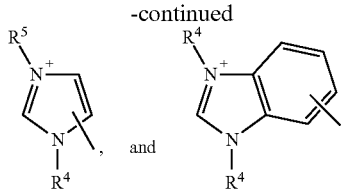

Equivalents of a suitable anion An⁻ are, for example, halides such as F⁻, Cl⁻, Br⁻ or I⁻, or anions derived from an inorganic acid, such as tetrafluoroborate, borate, perchlorate, nitrite, nitrate, phosphate, hydrogenphosphate, dihydrogenphosphate, carbonate, hydrogen carbonate, hydrogen sulfate, sulfate, or anions derived from an organic acid, such as a mono- or poly $C_1$-$C_{18}$carboxylic acid, or $C_1$-$C_{18}$alkoxy sulfate, aromatic or aliphatic sulfonate, or mixtures thereof.

Where Z is $SO_2R^9$; $SO_3R^9$; $SO_2NR^9R^{10}$; or $PO(OR^9)_2$, $R^9$ and $R^{10}$ are preferably H or $C_1$-$C_4$alkyl, preferably H.

Where Z is $SO_3^-Cat^+$, $Cat^+$ is an equivalent of a suitable cation, for example, alkali metal cations or alkaline earth metal cations, like $Na^+$, $K^+$, $\frac{1}{2}Ca^{2+}$, or an ammonium ion $N^+R^{17}R^{18}R^{19}R^{20}$, wherein $R^{17}$, $R^{18}$, $R^{19}$ and $R^{20}$ are independently from each other H, $C_1$-$C_{25}$alkyl, $C_3$-$C_{25}$alkenyl, $C_7$-$C_{25}$aralkyl or a chain consisting of 1, 2 or 3 members, each member independently of any other(s) being —$(CH_2)_2O$—, —$(CH_2)_3O$—, —$CH(CH_3)CH_2O$—, —$CH_2CH(CH_3)O$— or —$CH_2CH(CH_2O—)O$— and the chains being terminated by H, $CH_3$, $C_2H_5$ or $C(=O)CH_3$, for example, as described in WO 02/48268 and WO 02/48269.

Examples are ammonium, tetramethyl, tetrabutyl, methyltri(2-octyl)ammonium, di(2-hydroxyethyl)-methyl-(cis-9-octadecenyl)-ammonium, oleyl-bis(2-hydroxyethyl)methylammonium, and coco-bis(2-hydroxyethyl)methylammonium.

Halogen denotes I, Br, Cl, or F, preferably F on alkyl and Cl or Br on aryl.

The term "substituted" means "substituted one or more times with", that is 1 to 6 times, where possible, preferably 1 to 4 times, more preferably 1, 2 or 3 times. If a substituent occurs more than once in a group, it may be different in each occurrence.

The covalently bound carbon atom of the group of formula

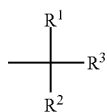

(III)

may be an aliphatic carbon atom, especially a tertiary carbon atom. Advantageously, the invention relates to a pigment preparation, wherein the covalently bound carbon atom of the group of formula (III) is a tertiary carbon atom.

Preferably, $R^1$ and $R^2$ are independently of each other methyl, ethyl, propyl, isobutyl, n-butyl, or CN, most preferably $R^1$ and $R^2$ are independently of each other methyl, ethyl, propyl, isobutyl, n-butyl, or $R^1$ is methyl and $R^2$ is CN. Of particular interest are pigment preparations, wherein $R^1$ and $R^2$ are methyl.

In a further preferred aspect the invention relates to a pigment preparation, wherein $R^1$ and $R^2$ are independently of each other $C_1$-$C_6$alkyl, preferably methyl or ethyl, or $R^1$ and $R^2$ together with the linking carbon atom form a 5 to 12 membered ring, said ring is unsubstituted or substituted with E and said ring may further contain one or more groups selected from —O—, —$NR^4$—, —$N(—OR^4)$—, or —$N^+R^4R^5$ An⁻;

$R^3$ is a group of formula

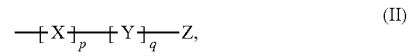

(II)

p and q are 0,
Z is $OR^9$; $OCOR^9$; CN; $NR^9R^{10}$; $N^+R^9R^{10}R^5$ An⁻; $C_6$-$C_{18}$aryl, said aryl is unsubstituted or substituted with E; $COOR^9$; $CONR^9R^{10}$;

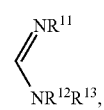

$SO_2R^9$; $SO_3R^9$; $SO_2NR^9R^{10}$, $SO_3^-Cat^+$; or $PO(OR^9)_2$; or a heterocyclic $C_2$-$C_{20}$ring system, said ring system contains one or more groups selected from O, S, N, $NR^4$, $NOR^4$, $N^+R^4R^5$ An⁻ or $N^+R^5$ An⁻, and said ring system is unsubstituted or substituted with E;

$R^9$, $R^{10}$, $R^{11}$, $R^{12}$ and $R^{13}$ are independently of each other and in each occurrence H, $C_1$-$C_{18}$alkyl, $C_3$-$C_8$alkenyl, $C_5$-$C_7$cycloalkyl, said alkyl, alkenyl or cycloalkyl is unsubstituted or substituted with D; $C_6$-$C_{18}$aryl, $C_7$-$C_{18}$aralkyl, said aryl in $C_6$-$C_{18}$aryl or $C_7$-$C_{18}$aralkyl is unsubstituted or substituted with E; or $R^9$ and $R^{10}$ together with the linking nitrogen atom form a 5 or 6 membered heterocyclic ring, said ring is unsubstituted or substituted with E, and said ring may further contain one or more groups selected from —O—, —$NR^4$— or —$N^+R^4R^5$ An⁻; or $R^{12}$ and $R^{13}$ together with the linking nitrogen atom form a 5 or 6 membered heterocyclic ring, said ring is unsubstituted or substituted with E, and said ring may further contain one or more groups selected from O, N, $NR^4$, $N^+R^4R^5$ An⁻ or $N^+R^5$ An⁻; or $R^{11}$ and $R^{12}$ together with the linking NCN group form a 5 or 6 membered cyclic amidine, said amidine is unsubstituted or substituted with E; and $R^4$, $R^5$, D, E, An⁻ and $Cat^+$ are defined as above. $R^4$ is preferably H, methyl, ethyl or 2-hydroxyethyl or 2-carboxyethyl.

In the pigment preparation described hereinbefore, more preferred groups of $R^9$, $R^{10}$, $R^{11}$, $R^{12}$, and $R^{13}$ are H, $C_1$-$C_8$alkyl, said alkyl may be substituted, and phenyl, said phenyl may be substituted. More preferred examples of the 5 or 6 membered heterocyclic ring, formed by $R^9$ and $R^{10}$, or $R^{12}$ and $R^{13}$ together with the nitrogen atom whereto they are bonded, may be derived from a saturated heterocyclic ring, such as imidazolidine, pyrrolidine, pyrazolidine, piperidine, piperazine, morpholine, which are unsubstituted or substituted one or more times with E.

If Z is

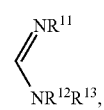

preferably, $R^{11}$ is H or methyl, and $R^{12}$ and $R^{13}$ are independently of each other H or $C_1$-$C_4$alkyl, said alkyl may be substituted with OH, COOH or $NH_2$, or $NMe_2$, or $R^{12}$ and $R^{13}$ form a heterocyclic group as defined hereinbefore.

Alternatively, Z may be a cyclic amidine, wherein $R^{11}$ and $R^{13}$ together with the linking NCN group form a 5 or 6 membered ring. Examples of cyclic amidines are

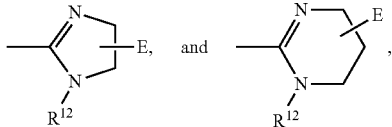

wherein $R^{12}$ may be H or $C_1$-$C_4$alkyl, which may be substituted with OH or COOH, for example, R is H, methyl, ethyl, propyl, butyl, 2-hydroxyethyl or 2-carboxyethyl; and E may be $C_1$-$C_4$alkyl or methoxy.

In a further preferred aspect the invention relates to a pigment preparation, wherein $R^1$ and $R^2$ are independently of each other $C_1$-$C_6$alkyl, preferably methyl, or CN, $R^3$ is a group of formula

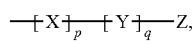 (II)

p and q are independently of each other 0 or 1, wherein the sum of p and q is 1 or 2;
X is —O—, —S—, —$NR^6$—, —$CONR^6$—, —OCO—, or —C(=$NR^7$)$NR^8$—;
Y is $C_1$-$C_{25}$alkylene, said alkylene may contain at the end or within the chain one or more groups selected from —O—, —S—, —CO—, —OCO—, —$CONR^6$—, —$NR^6$—, —$N^+R^6R^5$ cyclohexylene, phenylene, or naphthylene, and said alkylene may be substituted one or more times with Z;
Z is H; $OR^9$; $OCOR^9$; CN; $NR^9R^{10}$, —$N^+R^9R^{10}R^5$ $An^-$; $C_6$-$C_{18}$aryl, said aryl is unsubstituted or substituted with E; $COOR^9$; $CONR^9R^{10}$;

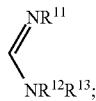

$SO_2R^9$; $SO_3R^9$; $SO_2NR^9R^{10}$, $SO_3^-Cat^+$; or $PO(OR^9)_2$; or a saturated or unsaturated heterocyclic $C_2$-$C_{20}$ring system, said ring system contains one or more groups selected from O, S, N, $NR^4$, $NOR^4$, $N^+R^4R^5$ $An^-$ or $N^+R^5$ $An^-$, and said ring system is unsubstituted or substituted with E;
$R^6$, $R^7$, $R^5$, $R^6$, $R^{10}$, $R^{11}$, $R^{12}$ and $R^{13}$ are independently of each other and in each occurrence H, $C_1$-$C_{18}$alkyl, $C_3$-$C_8$alkenyl, $C_6$-$C_7$cycloalkyl, said alkyl, alkenyl or cycloalkyl is unsubstituted or substituted with D, $C_6$-$C_{18}$aryl, $C_7$-$C_{18}$aralkyl, said aryl in $C_6$-$C_{18}$aryl or $C_7$-$C_{18}$aralkyl is unsubstituted or substituted with E; or
$R^9$ and $R^{10}$, or $R^{12}$ and $R^{13}$ together with the linking nitrogen atom form a 5 or 6 membered heterocyclic ring, said ring is unsubstituted or substituted with E, and said ring may further contain —O—, —$NR^4$— or —$N^+R^4R^5$ $An^-$-; or
$R^{11}$ and $R^{12}$ together with the linking NCN group form a 5 or 6 membered cyclic amidine, said amidine is unsubstituted or substituted with E; and
$R^4$, $R^5$, D, E, $An^-$ and $Cat^+$ are defined as above. $R^4$ is preferably H, methyl, ethyl, 2-hydroxyethyl or 2-carboxyethyl.

In the pigment preparation described hereinbefore, more preferred $R^1$ is CN and $R^2$ is methyl, $R^3$ is a group of formula

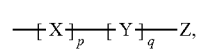 (II)

p is 0, and q is 1;
Y is $C_1$-$C_{25}$alkylene, said alkylene may contain at the end or within the chain one or more groups selected from —CO—, —COO—, —$CONR^6$—, —$NR^6$—, —$N^+R^6R^5$ $An^-$-, phenylene, or naphthylene;
Z is $OR^9$; $OCOR^9$; $NR^9R^{10}$, —$N^+R^9R^{10}R^5$ $An^-$; phenyl, biphenylyl, 1-naphthyl or 2-naphthyl, said phenyl, biphenylyl, 1-naphthyl or 2-naphthyl is unsubstituted or substituted with E; $COOR^9$; $CONR^9R^{10}$; $SO_3R^9$; $SO_2NR^9R^{10}$, $SO_3^-Cat^+$; or $PO(OR^9)_2$; or a saturated or unsaturated heterocyclic $C_2$-$C_{20}$ring system, said ring system contains one or more groups selected from O, S, N, $NR^4$, $NOR^4$, $N^+R^4R^5$ $An^-$ or $N^+R^5$ $An^-$; and is unsubstituted or substituted with E;
$R^6$, $R^9$, and $R^{10}$ are independently of each other and in each occurrence H, $C_1$-$C_4$alkyl, $C_3$-$C_5$alkenyl, $C_5$-$C_7$cycloalkyl, said alkyl, alkenyl or cycloalkyl is unsubstituted or substituted with D; phenyl, naphthyl, benzyl, phenetyl; or
$R^9$ and $R^{10}$ together with the linking nitrogen atom form a 5 or 6 membered heterocyclic ring, said ring is unsubstituted or substituted with E, and said ring may further contain —O—, —$NR^4$— or —$N^+R^4R^5$ $An^-$-; and
$R^4$, $R^5$, D, E, $An^-$ and $Cat^+$ are defined as above.

The pigment preparation described hereinbefore, is further more preferred, wherein $R^1$ and $R^2$ are methyl, $R^3$ is a group of formula

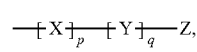 (II)

p and q are 1;
X is —$NR^6$—, —$CONR^6$—, or —COO—;
Y is $C_1$-$C_{25}$alkylene, said alkylene may contain at the end or within the chain one or more groups selected from —CO—, —COO—, —$CONR^6$—, —$NR^6$—, —$N^+R^6R^5$ $An^-$-, cyclohexylene, phenylene, or naphthylene, and said alkylene may be substituted one or more times with Z;
Z is $OR^9$; $OCOR^9$; CN; $NR^9R^{10}$, —$N^+R^9R^{10}R^5$ $An^-$; phenyl, naphthyl, said phenyl or naphthyl is unsubstituted or substituted with E; $COOR^9$; $CONR^9R^{10}$;

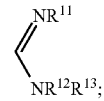

$SO_3R^9$; $SO_2NR^9R^{10}$, $SO_3^-Cat^+$; or $PO(OR^9)_2$; or a saturated or unsaturated heterocyclic $C_2$-$C_{20}$ring system, said ring system contains one or more groups selected from O, S, N, $NR^4$, $NOR^4$, $N^+R^4R^5$ $An^-$ or $N^+R^5$ $An^-$, and said ring system is unsubstituted or substituted with E;
$R^6$, $R^9$, $R^{10}$, $R^{11}$, $R^{12}$ and $R^{13}$ are independently of each other and in each occurrence H, $C_1$-$C_{18}$alkyl, $C_3$-$C_8$alkenyl, $C_5$-$C_7$cycloalkyl, said alkyl, alkenyl or cycloalkyl is unsubstituted or substituted with D, phenyl, naphthyl, benzyl, phenetyl, said aryl in phenyl, naphthyl, benzyl or phenetyl is unsubstituted or substituted with E; or $R^9$ and $R^{10}$, or $R^{12}$ and $R^{13}$ together with the linking nitrogen atom form a 5 or 6 membered heterocyclic ring, said ring is unsubstituted or substituted with E, and said ring may further contain —O—, —NR$^4$— or —N$^+$R$^4$R$^5$ An$^-$-; or $R^{11}$ and $R^{12}$ together with the linking NCN group form a 5 or 6 membered cyclic amidine, said amidine is unsubstituted or substituted with E; and $R^4$, $R^5$, D, E, An$^-$ and Cat$^+$ are defined as above.

Further preferred is a pigment preparation, wherein $R^1$ and $R^2$ are independently of each other methyl or ethyl, preferably methyl, $R^3$ is a group of formula

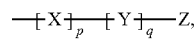
(II)

p is 1, and q is 1;
X is —CONR$^6$—, —COO— or —C(=NR$^7$)NR$^8$—;
Y is $C_1$-$C_6$alkylene, preferably ethylene, 1,3-propylene or 1,4-butylene;
Z is OR$^9$; OCOR$^9$; NR$^9$R$^{10}$ or —N$^+$R$^9$R$^{10}$R$^5$ An$^-$;
$R^6$, $R^7$, $R^8$, $R^9$, and $R^{10}$ are independently of each other and in each occurrence H, $C_1$-$C_{18}$alkyl, $C_3$-$C_8$alkenyl, $C_5$-$C_7$cycloalkyl, said alkyl, alkenyl or cycloalkyl is unsubstituted or substituted with D, $C_6$-$C_{18}$aryl, $C_7$-$C_{18}$aralkyl, said aryl is unsubstituted or substituted with E; or
$R^9$ and $R^{10}$ together with the linking nitrogen atom form a 5 or 6 membered heterocyclic ring, said ring is unsubstituted or substituted with E, and said ring may further contain —O—, —NR$^4$— or —N$^+$R$^4$R$^5$ An$^-$-; and
$R^4$, $R^5$, D, E, and An$^-$ are defined as above.

Further preferred is a pigment preparation, wherein $R^1$ and $R^2$ are methyl or ethyl, preferably methyl,
$R^3$ is a group of formula

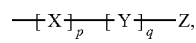
(II)

p is 1, and q is 1;
X is —CONR$^6$—, —COO—, or —C(=NR$^7$)NR$^8$—;
Y is $C_1$-$C_{25}$alkylene, said alkylene may contain at the end or within the chain one or more groups selected from —O—, —CO—, —COO—, —CONR$^6$—, —NR$^6$—, —N$^+$R$^6$R$^5$ An$^-$-;
Z is phenyl, naphthyl, said phenyl or naphthyl is unsubstituted or substituted with E; or a saturated heterocyclic $C_2$-$C_{20}$ring system or $C_2$-$C_{18}$hetaryl ring system, said ring system contains one or more groups selected from O, S, N, NR$^4$, NOR$^4$, N$^+$R$^4$R$^5$ An$^-$ or N$^+$R$^5$ An$^-$, and said ring system is unsubstituted or substituted with E;
$R^6$, $R^7$ and $R^8$ are independently of each other and in each occurrence H or $C_1$-$C_{18}$alkyl; and
$R^4$, $R^5$, E, and An$^-$ are defined as above.

Especially preferred is a pigment preparation, wherein R, and $R^2$ are methyl or ethyl, preferably methyl,
$R^3$ is a group of formula

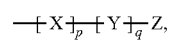
(II)

p is 1 and q is 1;
X is —CONR$^6$—, —COO—, or —C(=NR$^7$)NR$^8$—;
Y is $C_1$-$C_6$alkylene, said alkylene contains at the end a group of —CO—, —COO— or —CONR$^6$—;
Z is phenyl, naphthyl, said phenyl or naphthyl is unsubstituted or substituted with E; or a saturated heterocyclic $C_2$-$C_{20}$ring system or $C_2$-$C_{18}$hetaryl ring system, preferably a mono- or bicyclic system containing —NR$^4$— or —N(OR$^4$)—, or 4-pyridyl or

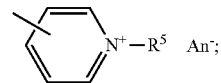

$R^4$, $R^5$, $R^6$, $R^7$ and $R^8$ are independently of each other and in each occurrence H or $C_1$-$C_{18}$alkyl; and An$^-$ is defined as above.

Especially preferred is also a pigment preparation, wherein $R^1$ and $R^2$ are independently of each other methyl,
$R^3$ is a group of formula

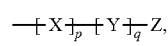
(II)

p is 1 and q is 1;
X is —CONR$^6$—, —COO— or —C(=NR$^7$)NR$^8$—;
Y is $C_1$-$C_6$alkylene, preferably ethylene, 1,3-propylene or 1,4-butylene;
Z is OR$^9$; OCOR$^9$; NR$^9$R$^{10}$ or —N$^+$R$^9$R$^{10}$R$^5$ An$^-$;
$R^6$, $R^7$, $R^8$, $R^9$, and $R^{10}$ are independently of each other and in each occurrence H, $C_1$-$C_{18}$alkyl, or phenyl, said phenyl is unsubstituted or substituted with E; and
$R^5$ and An$^-$ are defined as above.

Further preferred is a pigment preparation as described in any aspects before, wherein Z is SO$_2$R$^9$; SO$_3$R$^9$; SO$_2$NR$^9$R$^{10}$, SO$_3^-$Cat$^+$; or PO(OR$^9$)$_2$,
wherein $R^9$ and $R^{10}$ are independently of each other H or $C_1$-$C_{18}$alkyl, and
An$^-$ and Cat$^+$ are defined as above.

Suitable groups of formula

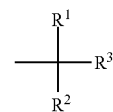
(III)

may, for example, groups which impart more hydrophobic properties to the pigment preparation.

Accordingly, in a further preferred aspect the invention relates to a pigment preparation, wherein $R^1$ and $R^2$ are independently of each other $C_1$-$C_6$alkyl, or
$R^1$ and $R^2$ together with the linking carbon atom form a 5 to 12 membered alicyclic ring, said ring is unsubstituted or substituted with E;
$R^3$ is $C_1$-$C_{25}$alkyl, $C_3$-$C_{25}$alkenyl, said alkyl or alkenyl is unsubstituted or substituted with D, $C_7$-$C_{25}$aralkyl, said aryl group in $C_7$-$C_{25}$aralkyl is unsubstituted or substituted with E, and D and E are independently from each other $C_1$-$C_4$alkyl.

If desired, the compound of component (b) can be extracted from the reaction mixture with a suitable solvent and re-precipitated, but it is in general more efficient to use them in the form of pigment preparations as obtained.

Hence, the invention also relates to a compound of formula

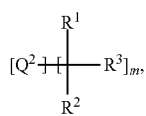
(I)

wherein $Q^2$ is a m-valent residue of chromophore $Q^1$ comprised in an organic pigment selected from bis(anthraquinone-1-yl-amino), bis(anthraquinone-1-yl-oxy), 1,1'-dianthraquinolyl, diketopyrrolopyrrole, indanthrone, isoindoline, isoindolinone, perylene, 1-phenylhydrazono-2-oxy-3-carbamoyl-1,2-dihydronaphthalene, quinacridone pigments, or a mixture of said pigments, including a solid solution or a mixed crystal;

$R^1$ and $R^2$ are independently of each other CN, $C_1$-$C_6$alkyl, $C_3$-$C_7$cycloalkyl, said alkyl or cycloalkyl is unsubstituted or substituted with D, $C_6$-$C_{10}$aryl, said aryl is unsubstituted or substituted with E; or $R^1$ and $R^2$ together with the linking carbon atom form a 5 to 12 membered ring, said ring is unsubstituted or substituted with E and said ring may further contain one or more groups selected from —O—, —NR$^4$—, —N(—OR$^4$)—, or —N$^+$R$^4$R$^5$ An$^-$—;

$R^3$ is $C_1$-$C_{25}$alkyl, $C_3$-$C_{25}$alkenyl, said alkyl or alkenyl is unsubstituted or substituted with D, $C_7$-$C_{25}$aralkyl, said aryl group in $C_7$-$C_{18}$aralkyl is unsubstituted or substituted with E, or a group of formula

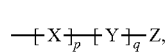
(II)

p and q are independently of each other 0 or 1;
X is —O—, —S—, —NR$^6$—, —CONR$^6$—, —COO—, or —C(=NR$^7$)NR$^8$—;
Y is $C_1$-$C_{25}$alkylene, said alkylene may contain at the end or within the chain one or more groups selected from —O—, —S—, —CO—, —COO—, —CONR$^6$—, —NR$^6$—, —N$^+$R$^6$R$^5$ An$^-$—, an alicyclic or aromatic ring, and said alkylene may be substituted one or more times with Z;
Z is H; OR$^9$; OCOR$^9$; CN; NR$^9$R$^{10}$, —N$^+$R$^9$R$^{10}$R$^5$ An$^-$; $C_6$-$C_{10}$aryl, said aryl is unsubstituted or substituted with E; COOR$^9$; CONR$^9$R$^{10}$;

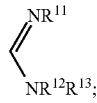

SO$_2$R$^9$; SO$_3$R$^9$; SO$_2$NR$^9$R$^{10}$, SO$_3$Cat$^+$; or PO(OR$^9$)$_2$; or a heterocyclic $C_2$-$C_{20}$ring system, said ring system contains one or more groups selected from O, S, N, NR$^4$, NOR$^4$, N$^+$R$^4$R$^5$ An$^-$ or N$^+$R$^5$ An$^-$, and said ring system is unsubstituted or substituted with E;

$R^4$ is H or $C_1$-$C_4$alkyl, said alkyl is unsubstituted or substituted with D;
$R^5$ is H, $C_1$-$C_4$alkyl, $C_7$-$C_{10}$aralkyl or $C_3$-$C_5$alkenyl;
$R^6$, $R^7$, $R^8$, $R^9$, $R^{10}$, $R^{11}$, $R^{12}$ and $R^{13}$ are independently of each other and in each occurrence H, $C_1$-$C_{18}$alkyl, $C_3$-$C_{18}$alkenyl, $C_5$-$C_{12}$cycloalkyl, said alkyl, alkenyl or cycloalkyl is unsubstituted or substituted with D; $C_6$-$C_{18}$aryl, $C_7$-$C_{18}$aralkyl, said aryl in $C_6$-$C_{18}$aryl or $C_7$-$C_{18}$aralkyl is unsubstituted or substituted with E; or
$R^9$ and $R^{10}$ together with the linking nitrogen atom form a 5 to 7 membered heterocyclic ring, said ring is unsubstituted or substituted with E, and said ring may further contain one or more groups selected from —O—, —NR$^4$— or —N$^+$R$^4$R$^5$ An$^-$—; or
$R^{12}$ and $R^{13}$ together with the linking nitrogen atom form a 5 to 7 membered heterocyclic ring, said ring is unsubstituted or substituted with E, and said ring may further contain one or more groups selected from O, N, NR$^4$, N$^+$R$^4$R$^5$ An$^-$ or N$^+$R$^5$ An$^-$; or
$R^{11}$ and $R^{12}$ together with the linking NCN group form a 5 to 7 membered cyclic amidine, said amidine is unsubstituted or substituted with E;
E is $C_1$-$C_4$alkyl, $C_1$-$C_4$alkoxy, COOH, OH, halogen, NR$^9$R$^{10}$, —N$^+$R$^9$R$^{10}$R$^5$ An$^-$, SO$_3$R$^9$, SO$_2$NR$^9$R$^{10}$ or SO$_3$Cat$^+$;
D is $C_1$-$C_4$alkoxy, OH, COOH, or halogen;
An$^-$ is an equivalent of a suitable anion;
Cat$^+$ is an equivalent of a suitable cation;
m is an integer from 1 to 4; and
each group of formula

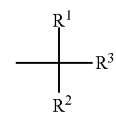
(III)

is selected independently of the others.

Typically, the chromophore $Q^2$ comprises at least one group of formula

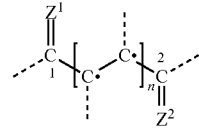
(X)

or a cis/trans isomer thereof, wherein $Z^1$ and $Z^2$ are independently of each other O or N—, each C• is independently of all other C• a carbon atom with an electron in a p orbital, and n is an integer from 1 to 4.

The instant pigment preparation may be prepared by treating a suspension of an organic pigment comprising a chromophore $Q^1$ with a radical of formula

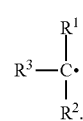
(IV)

Accordingly, the invention relates to a process, which process comprises the step of treating a suspension of an organic pigment comprising a chromophore $Q^1$ with a radical of formula

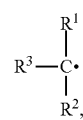
(IV)

wherein $R^1$, $R^2$ and $R^3$ are defined as above.

Usually, the radical of formula (IV) may be generated in situ by decomposing a suitable treating agent by heat or irradiation, preferably by heat.

A suitable treating agent may be an azo or peroxy compound or a combination of a suitable iodide with benzoyl peroxide, preferably an azo or peroxy compound. For example, the radical of formula (IV) may be prepared by decomposing the following azo compound:

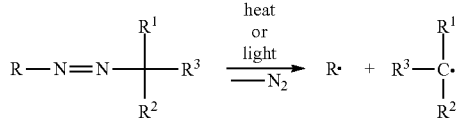

A suitable azo compound may be of formula

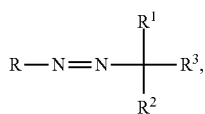
(VIa)

wherein R is a group of formula

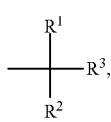
(III)

phenyl, triphenylmethyl, or $CONR^{15}R^{16}$, wherein $R^{15}$ and $R^{16}$ are independently of each other H, $C_1$-$C_4$alkyl or

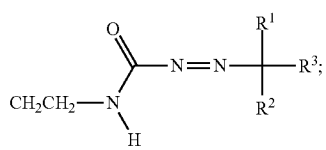

each group of

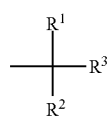
(III)

is selected independently of the other; and
$R^1$, $R^2$, and $R^3$ are independently of each other as defined above.

A symmetrical azo compound of formula

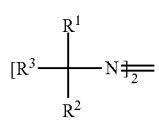
(V)

is preferred.

Alternatively, peroxy compounds such as diacyl peroxides (R—CO—O—O—CO—R) or peresters (R—CO—O—O—R', wherein R corresponds to the organic group to be linked to the chromophore) can be used as source of free radicals (IV). Particularly suitable peroxy compounds are diacylperoxides of formula (XI), wherein $R^1$, $R^2$ and $R^3$ are independently of each other as defined above.

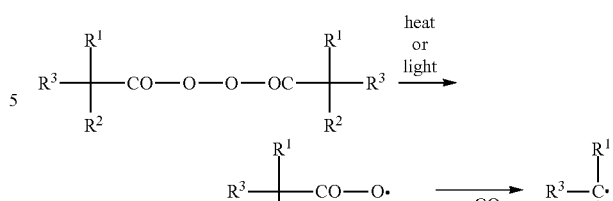

Further, benzoylperoxide may be used in connection with an organic iodide of formula

(XII)

wherein the iodide is the source of the radical to be attached.

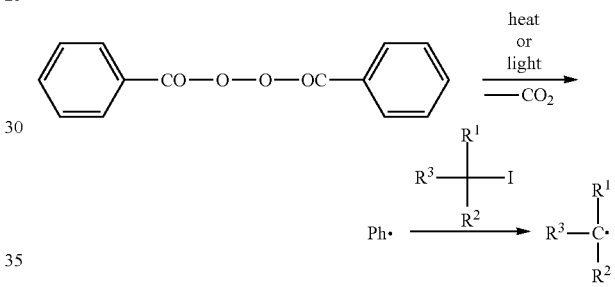

Likewise, a radical of formula (IV) may be prepared from an iodide of formula (XII) using a methyl radical generated from dimethyl sulfoxide with iron(II)oxide and hydrogen peroxide.

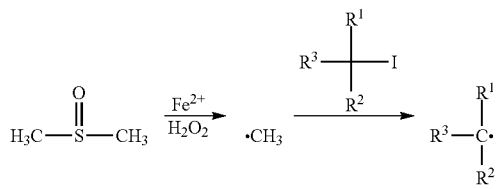

A variety of azo compounds are commercially available. They may also be prepared according to methods described, for example, by Overberger, H. et al., J. Am. Chem. Soc., 71(8), 1949, 2661, wherein symmetrical azoinitiators are described. Asymmetric alkyl-acyl azoinitiators are, for example, described by Lynch, T. R., et al., Canad. J. Chem., 49(10), 1971, 1598. Asymmetric alkyl-aminocarbonyl azoinitiators can be prepared in analogy to Comanita, E., et al., Polymer Bulletin, 31(1), 1993, 15. Asymmetric alkyl-aryl azoinitiators can be prepared as described, for example, by Okimoto, M. et al., Synthesis, 13, 2003, 2057.

A comprehensive treatment of all aspects of these materials, e.g., synthesis, mechanism of decomposition, is given in "Handbook of Free Radical Initiators" (E. T. Denisov, T. G. Denisova, T. S. Pokidova, Wiley-Interscience, 2003).

Further, the invention relates to an azo compound of formula

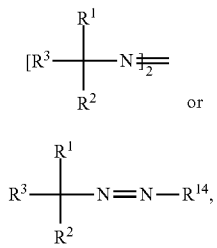

wherein
$R^1$ and $R^2$ together with the linking carbon atom form a 8 to 12 membered ring, said ring is unsubstituted or substituted with E, or a 5 to 7 membered ring, said ring is unsubstituted or substituted with E, and said ring contains one or more groups of $-N(-OR^4)-$;
$R^3$ is CN; and
$R^{14}$ is phenyl, triphenylmethyl, or $CONR^{15}R^{16}$, wherein $R^{15}$ and $R^{16}$ are independently of each other H, $C_1$-$C_4$alkyl or

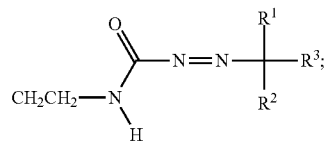

or
an azo compound of formula (V), wherein
$R^1$ and $R^2$ are independently of each other CN, $C_1$-$C_6$alkyl, or $C_3$-$C_7$cycloalkyl, said alkyl or cycloalkyl is unsubstituted or substituted with D, $C_6$-$C_{18}$aryl, said aryl is unsubstituted or substituted with E;
$R^3$ is a group of formula

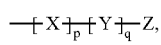

p and q are independently of each other 0 or 1;
X is $CONR^6-$, $-COO-$, or $-C(=NR^7)NR^8-$;
Y is $C_1$-$C_{25}$alkylene, said alkylene may contain at the end or within the chain one or more groups selected from $-O-$, $-S-$, $-CO-$, $-COO-$, $CONR^6-$, $-NR^6-$, $-N^+R^6R^5 An^--$, an alicyclic or aromatic ring, and said alkylene may be substituted one or more times with Z;
Z is $SO_2R^9$; $SO_3R^9$; $SO_2NR^9R^{10}$, $SO_3^-Cat^+$; $PO(OR^9)_2$; a saturated heterocyclic $C_2$-$C_{20}$ring system, said ring system contains one or more groups selected from $NR^4$, $NOR^4$, $N^+R^4R^5 An^-$ or $N^+R^5 An^-$, and said ring system is unsubstituted or substituted with E; or $C_2$-$C_{18}$heteroaryl;
$R^4$ is H or $C_1$-$C_4$alkyl, said alkyl is unsubstituted or substituted with D;
$R^5$ is H, $C_1$-$C_4$alkyl, $C_7$-$C_{10}$aralkyl or $C_3$-$C_5$alkenyl;
$R^6$, $R^7$, $R^8$, $R^9$, and $R^{10}$ are independently of each other and in each occurrence H, $C_1$-$C_{18}$alkyl, $C_3$-$C_{18}$alkenyl, $C_5$-$C_{12}$cycloalkyl, said alkyl, alkenyl or cycloalkyl is unsubstituted or substituted with D, $C_6$-$C_{18}$aryl, $C_7$-$C_{18}$aralkyl, said aryl is unsubstituted or substituted with E;

E is $C_1$-$C_4$alkyl, $C_1$-$C_4$alkoxy, COOH, OH, halogen, $NR^9R^{10}$, $-N^+R^9R^{10}R^5 An^-$, $SO_3R^9$, $SO_2NR^9R^{10}$ or $SO_3^-Cat^+$;
D is $C_1$-$C_4$alkoxy, OH, COOH, or halogen;
$An^-$ is an equivalent of a suitable anion; and
$Cat^+$ is an equivalent of a suitable cation.

Suitable examples of azo compounds for the preparation of the pigment preparation of the invention are given in Table 1.

TABLE 1

| Examples of azo compounds |
|---|
| 1 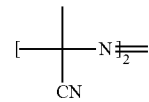 |
| 2 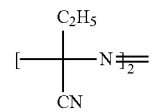 |
| 3 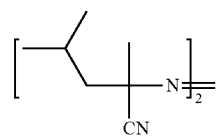 |
| 4 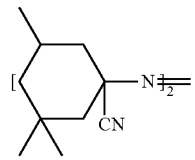 |
| 5 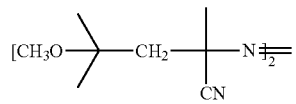 |
| 6 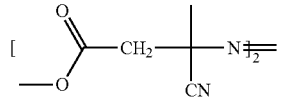 |
| 7 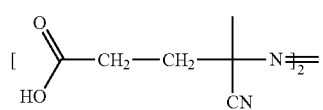 |
| 8 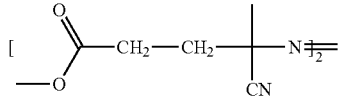 |
| 9 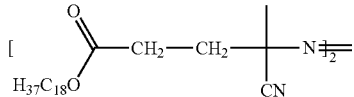 |
| 10 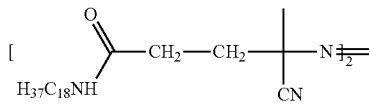 |

TABLE 1-continued
Examples of azo compounds
| 11 | 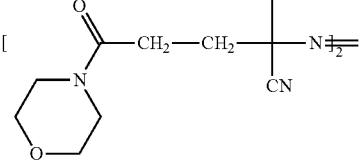 [SMILES: C=NC(C)(C#N)CCC(=O)N1CCOCC1] |
| 12 | 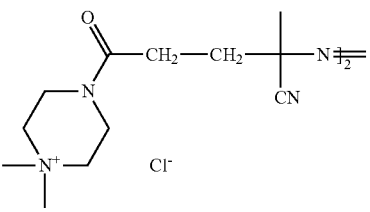 |
| 13 | 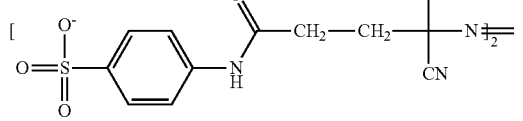 |
| 14 | 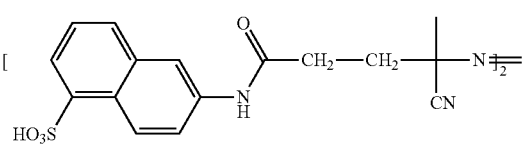 [SMILES: C=NC(C)(C#N)CCC(=O)Nc1ccc2c(S(=O)(=O)O)cccc2c1] |
| 15 | 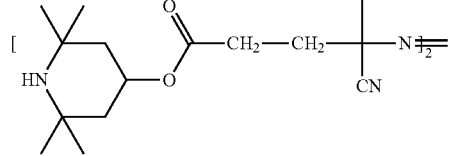 [SMILES: C=NC(C)(C#N)CCC(=O)OC1CC(C)(C)NC(C)(C)C1] |
| 16 | 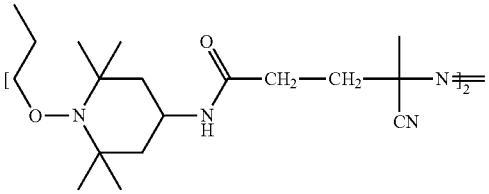 [SMILES: C=NC(C)(C#N)CCC(=O)NC1CC(C)(C)N(OCCC)C(C)(C)C1] |
| 17 | 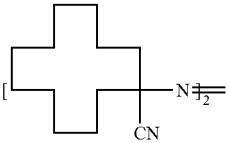 |
| 18 | 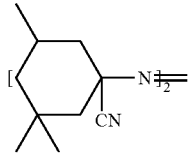 |
| 19 | 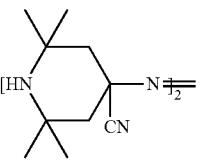 |
| 20 | 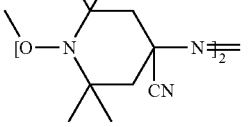 |
| 21 | 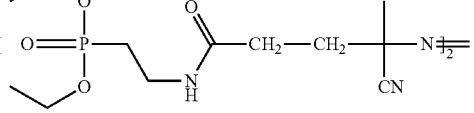 |
| 22 | 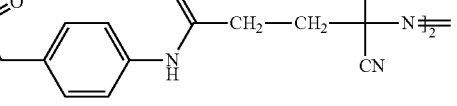 |
| 23 | 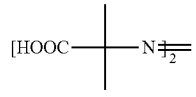 |
| 24 | 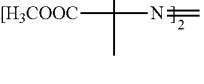 |
| 25 |  |
| 26 | 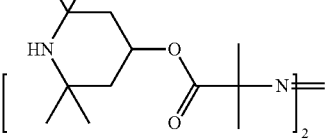 |
| 27 | 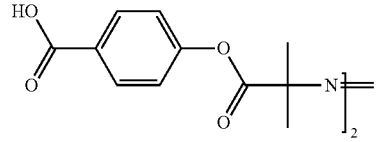 |
| 28 | 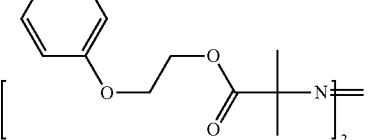 |
| 29 | 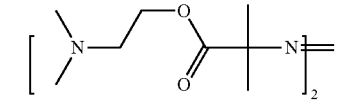 |

TABLE 1-continued

Examples of azo compounds

30–48: (chemical structures)

TABLE 1-continued

Examples of azo compounds

TABLE 1-continued

Examples of azo compounds

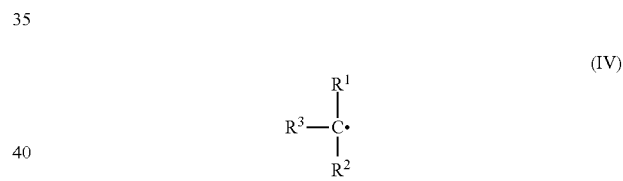

Many peroxides are also commercially available or may be prepared according to methods described, for example, by Rappoport, Z., (ed), The Chemistry of Peroxides. Vol. 2, Parts 1-2, John Wiley & Sons Ltd, Chichester, UK, 2006. Suitable examples of diacylperoxides or peresters are given in Tables 2 and 3.

TABLE 2

Examples of diacylperoxides (R—CO—O—O—CO—R)

TABLE 3

Examples of peresters R—CO—O—O—R' (R corresponds to the organic group to be linked to the chromophore)

Usually, a 5 to 15% by weight suspension, preferably 5 to 10% by weight, based on the total weight of the suspension, of an organic pigment (a) in an aqueous or organic medium is obtained by subjecting the pigment, as a powder or a presscake in water, normally to high shearing in order to reduce the particle size distribution of the pigment to a desired size. Said suspension may then be treated with a suitable treating agent, for example, an azo or peroxy compound, whereby a radical of formula $$R^3-\underset{\underset{R^2}{|}}{\overset{\overset{R^1}{|}}{C}}\cdot \qquad (IV)$$

may be generated by exposing the suspension to irradiation or by treating the suspension at a predetermined temperature. Of course, a mixture of azo compounds or a mixture of peroxy compounds may be used. It may also be suitable to add the treating agents, alone or usually dissolved in the reaction medium, in one or more portions to the suspension. The resulting pigment preparation may be purified using techniques known skilled in the art, for example, filtration, centrifugation or a combination thereof to remove unreacted raw materials, byproducts and other reaction impurities.

The temperature is not specifically restricted, however, too low temperature retards the process for surface modification due to less decomposition of the treating agent, whereas too high temperature causes too rapid decomposition of the radical precursor which may lead to loss of reaction control or inefficient grafting due to undesired side reactions such as a combination of the free radicals. Therefore, the temperature is usually of from 20 to 150° C., and preferably from 30 to 100° C.

The reaction time depends on reaction conditions such as temperature and kind or concentration of the treating agent, and is usually from 0.5 or less to about 24 hours or more.

The thermal decomposition of azoinitiators or peroxides follows first order kinetic ($-d[I]/dt=k_d[I]$), wherein $k_d$ is the rate constant of initiator decomposition. The temperature dependency of $k_d$ obeys the Arrhenius relationship ($k_d = Ae^{-(E_a/RT)}$). According to $t_{1/2} = \ln 2/k_d$, the half life time ($t_{1/2}$) may be calculated.

Preferably, time and temperature are chosen as a function of the half life time ($t_{1/2}$) of the azo- or peroxy-compound which is the time required reducing the original amount of the initiator by 50% at a given temperature. Thus, selecting the reaction time as a multiple, for example, 3 to 10 of ($t_{1/2}$) will ensure near complete or complete conversion of the free radical source. The half life times of initiators are tabulated, for example, in "Polymer Handbook", 4$^{th}$ ed., Editors: J. Brandrup, E. A. Immergut, A. Abe, D. R. Bloch, © 1999; 2005 John Wiley & Sons).

An aqueous medium may be water or mixture of water with a water-miscible solvent. Suitable water-miscible solvents are acetonitrile, alcohols like ethanol, methanol, 1-propanol, 2-propanol, 1-methoxy-2-propanol, ethylene glycol, diethylene glycol, tetrahydrofurane (THF), dioxane, pyridine, N-methylpyrrolidone (NMP), dimethylformamide (DMF), or dimethylacetamide (DMA). Also mixtures of solvents can be used. Naturally, other solvents can be used as long as they do not interfere negatively with the reaction. In case the treating agent is soluble in water, water is preferred.

An organic medium may be an organic solvent or a mixture of organic solvents. Any organic solvent may be used, for example, the water-miscible solvents defined above, or hydrocarbons such as pentane, hexane, cyclohexane, dodecane, toluene, and the like.

The treating agent is adequately used in amount half of the stoichiometric amount or in slight or large excess, for example, up to 5 times of the stoichiometric amount, preferably about from 2 to 3 times the stoichiometric amount, based on the desired amount of compound of formula (I). The optimal amount depends somewhat on the pigment to be substituted and may in any case easily be determined experimentally.

The organic group may be attached to the pigment in varying amounts. The amount to be attached may be varied in order to obtain the desired performance attributes, for example, dispersibility in a hydrocarbon solvent and/or dispersibility in a polymeric resin or binder. In addition, modified pigment preparations may comprise multiple attached organic groups, which may result in improved properties.

In general, the amount of compound of formula (I) is of from 0.1 to 30 mol, based on 100 mol of the organic pigment (a), preferably 0.5 to 25 mol, more preferred 0.8 to 15 mol and most preferred 1 to 10 mol.

The inventive pigment preparations may also be subsequently functionalized. Suitable groups of component (b), for example an OH group, a NH$_2$ group, a COOH group, a halogen, may be further derivatized, such as etherification, alkylation, esterification, by reaction with thionyl chloride and long-chain amines, and the like. Further functionalization may result in pigment preparation wherein one or more compounds of formula

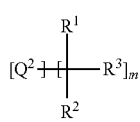

(I)

are present.

The pigment preparations of the invention may be used as solid systems of free-flowing, pulverulent consistency, as granules, or as aqueous presscake, preferably as powder or granules.

The pigment preparations of the invention may further comprise suitable additives, such as surfactants, dispersants, resins, waxes, fillers, defoamers, antidust agents, extenders, shading colorants, preservatives, dryness retarders, rheology control additives, wetting agents, antioxidants, UV absorbers, light stabilizers or combinations mixtures thereof.

Preferred pigment preparations consist essentially of components (a) and (b). The additives may be present of from 0 to 20% by weight, preferably 0-10% by weight, based on the total weight of components (a) and (b).

The pigment preparations of the invention may be used in the same applications as conventional pigments. The groups attached to the pigment surface, however, may be used to modify and improve the properties of a given pigment for a particular use. The pigment preparations of the invention may be used in a number of applications.

The pigment preparations according to the invention are employed in general by methods known per se in high molecular weight organic material, for example, a) for mass coloring polymers, e.g. in the form of resins or plastics including fibers;

b) for the preparation of paints, paint systems, coating compositions, for example, in automotive coatings, paper colors, printing colors, inks including ink-jet applications and writing purposes, as well as for toners in electrophotography, e.g. for laser printers;

c) for photoresists for color filters (polymer/paint formulation for displays, electronic applications);

d) as an additive to colorants, such as pigments and dyes; and the like.

For example, the pigment preparations of the present invention are particularly suitable for pigmenting plastics, surface coatings and printing inks, especially in coating and ink applications. Accordingly, the invention relates to the use of the instant pigment preparations for pigmenting plastics, coating compositions and printing inks.

In a further aspect, the invention relates to a colored or pigmented composition comprising a an organic material, preferably a high molecular weight organic material, and 0.01 to 70% by weight, based on the weight of the high molecular weight organic material, of a pigment preparation as described in any aspects hereinabove.

Preferably, the invention relates to a mass-colored high molecular weight organic material comprising
a high molecular weight organic material, and
0.01 to 70% by weight, based on the weight of the high molecular weight organic material, of a pigment preparation as described in any aspects above.

The organic material, preferably a high molecular weight organic material, to be colored in accordance with the invention can be of natural or synthetic origin and usually has a molecular weight in the range of from 10$^3$ to 10$^8$ g/mol. It may be, for example, a natural resin or a drying oil, rubber or casein, or a modified natural substance, such as chlorinated rubber, an oil-modified alkyd resin, viscose, or a cellulose ether or ester, such as cellulose acetate, cellulose propionate, cellulose acetobutyrate or nitrocellulose, but is especially a completely synthetic organic polymer (either thermosetting plastics or thermoplastics), as are obtained by polymerisation, polycondensation or polyaddition, for example polycarbonate, polyester, such as polyethylene terephthalate or polybutylene terephthalate, polyolefins, such as polyethylene (HDPE, HDPE-HMW, HDPE-UHMW, LDPE, LLDPE, VLDPE, ULDPE), polypropylene or poly-isobutylene, substituted polyolefins, such as polymerisation products of vinyl chloride, vinyl acetate, styrene, acrylonitrile or acrylic acid and/or methacrylic acid esters, or butadiene, polystyrene or polymethyl methacrylate, and also copolymerisation products of the said monomers, especially acrylonitrile/butadiene/styrene (ABS), styrene/acrylonitrile (SAN) or EVA.

Polyaddition resins and polycondensation resins may be condensation products of formaldehyde with phenols, so-called phenoplasts, and condensation products of formaldehyde with urea, thiourea and melamine, so-called aminoplasts, the polyesters used as coating resins, either saturated, such as alkyd resins, or unsaturated, such as maleic resins, and also linear polyesters and polyamides or silicones.

Said high molecular weight material may be present individually or in mixtures, in the form of plastic compositions, solutions or melts which can, if desired, be spun into fibers. It may also be in the form of its monomers or in the polymerized state in dissolved form as film formers or binders for surface coatings or for printing inks, such as boiled linseed oil, nitrocellulose, alkyd resins, melamine resins, urea-formaldehyde resins, acrylic resins. Multilayer systems are possible, too.

Pigmenting a high molecular weight organic material with the pigment preparations of the invention is effected, for example, by admixing said pigment preparation, optionally in the form of a masterbatch, with the substrates using roll mills or mixing or grinding apparatus. The pigmented material is then generally brought into its desired final form by processes known per se, such as calendering, compression molding, extrusion, spread-coating, casting or injection-molding. It is often desirable, in order to produce non-rigid moldings or to reduce their brittleness, to incorporate so-called plasticizers in the high molecular weight material prior to shaping. Examples of plasticizers are esters of phosphoric acid, phthalic acid or of sebacic acid. In the process of the invention, plasticizers may be incorporated into the polymers before or after the pigment preparation. In order to obtain different color shades, it is also possible to add to the high molecular weight organic materials fillers or other color-imparting constituents, such as white, colored or black pigments as well as effect pigments, in each case in the desired amount.

The pigment preparation of the invention can especially be used in pigmenting partially crystalline plastics, especially those processed by injection-molding, without the occurrence of warping. In the plastics processing industry "warping" is a known major problem observed in partially crystalline plastics following injection-molding, more especially in the presence of organic pigments.

"Partially crystalline plastics" are to be understood as meaning those plastics that on solidification form small crystalline nuclei or aggregates (for example spherulites or quadrites), including plastics that exhibit such behaviour only in the presence of nucleating agents (for example, organic pigments). Partially crystalline plastics are generally thermoplastic high molecular weight organic materials having a molecular weight ($M_w$) of from $10^4$ to $10^8$ g/mol, especially from $10^5$ to $10^7$, and a degree of crystallinity ($X_c$) of from 10 to 99.9%, preferably from 40 to 99%, especially from 80% to 99%. Preferred partially crystalline plastics are homopolymers, block or random copolymers and terpolymers of ethylene, propylene, butylene, styrene and/or divinylbenzene, especially α-olefins, such as HDPE, LDPE, polypropylene and polystyrene, and also polyesters, such as PET, polyamides, such as nylon 6 and nylon 66, and thermoplastic ionomers. Especially preferred partially crystalline plastics are polyolefins, especially polyethylene of high density and polypropylene. The partially crystalline plastics may optionally comprise customary amounts of additives, for example, stabilisers, optical brighteners, fillers and/or lubricants.

The invention accordingly relates also to a composition comprising a partially crystalline plastics and a pigment preparation, as described above.

The influence on the warpage tendency of polyolefin by the pigment preparation is tested on a ready-produced injection molding in the form of a panel in accordance with DIN EN ISO 294-4:2003. After aging, the dimensions of the panel (length, width) are measured and the degree of the warpage is determined.

The preparation is carried out according to customary processes, for example, by mixing the pigment preparation of the invention with the plastics granules or powder, and extruding the mixture to form fibers, films or granules. The latter can then be formed into articles, e.g., by injection-molding, such articles exhibiting scarcely any warping on solidification or in many cases no warping at all. Where appropriate, of course, additives may also be used in customary manner as further additional ingredients.

The pigment preparations of the invention are preferably used in surface coatings, especially in solvent-based automotive finishes, where they make a higher pigment content possible.

For pigmenting a surface coating, paint systems and printing ink, the high molecular weight organic materials and the pigment preparation of the invention are finely dispersed or dissolved, optionally together with additives, such as stabilizers, dispersants, gloss improvers, fillers, other pigments or dyes, siccatives or plasticizers, generally in an organic and/or aqueous solvent or solvent mixture. Individual components may also be dispersed or dissolved separately, or a plurality thereof may be dispersed or dissolved together, and only then are all of the components combined.

Accordingly, a preferred embodiment is a composition, wherein the composition is a coating composition and the high molecular weight organic material is an organic film-forming binder.

More preferred is a coating composition, comprising from 0 to 50% by weight, preferably from 5 to 30% by weight of a volatile part, based on the total weight of the composition, from 10 to 50% by weight of a non-volatile, essentially colorless part, based on the total weight of the composition, and from 5 to 85% by weight, based on the total weight of the composition, of a colorant part comprising an organic pigment comprising a chromophore $Q^1$,
wherein said coating composition also comprises from 0.1 to 30 mol, preferably 0.5 to 25 mol, more preferred 0.8 to 15 mol and most preferred 1 to 10 mol, based on 100 moles of said organic pigment, of a compound comprising a chromophore of the formula

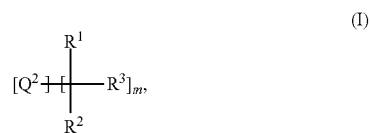

(I)

wherein $Q^2$ is a m-valent residue of chromophore $Q^1$;
and m, $R^1$, $R^2$, and $R^3$ are defined in any aspect as defined above.

The volatile part of the coating composition is the part which vanishes from the coating upon curing. The non-volatile part comprises binders and/or binder precursors and, if desired additives, such as photo initiators, stabilizers (e.g., antioxidants, UV absorbers, photo stabilizers, rheology modifiers, glossing agents), inorganic white or effect pigments (e.g., titanium dioxide, mica or aluminum flakes) and/or fillers. Binder precursors are compounds which react upon curing to form a binder (in general unsaturated monomers and telomers). Essentially colorless should be understood as excluding compounds having a molar absorption coefficient $K_n \geq 5000$ $l \cdot mol^{-1} \cdot cm^{-1}$ at any wavelength in the range from 400 to 700 nm, especially colorants, such as those listed in the Color Index.

The colorant part may consist essentially of one or more organic pigments comprising a chromophore $Q_1$, or it may also comprise further colorants, such as partially or fully soluble dyes or particularly preferred inorganic black or color pigments and/or organic pigments having different chromophores. The purpose of optionally adding additional colorants is in general to adjust the hue, chroma and/or transparency or opacity, to generate a special effect (such as goniochromaticity and/or angular reflectivity), or to optimize the cost efficiency of the coating composition.

Coating compositions typically comprise a polymeric binder which may in principle be any binder customary in industry. In general, it is a film forming binder based on a thermoplastic or thermosetting resin, for example a thermosetting resin.

Examples of organic film-forming binders are epoxy resins, polyurethane resins, amino resins, acrylic resins, acrylic copolymer resins, polyvinyl resins, phenolic resins, styrene/butadiene copolymer resins, vinyl/acrylic copolymer resins, polyester resins, UV-curable resins or alkyd resins, or a mixture of two or more of these resins, or an aqueous basic or acidic dispersion of these resins or mixtures of these resins, or an aqueous emulsion of these resins or mixtures of these resins. Provided the binders are curable binders, they are normally used together with a hardener and/or accelerator.

For example, compositions for coatings or films comprising acrylate polymers are useful in the instant invention. Acrylic, methacrylic and acrylamide polymers and co-polymers dispersible in water may also readily be used as a binder in the present invention.

The coating composition can also comprise further components, examples being solvents, pigments, dyes, plasticizers, stabilizers, thixotropic agents, drying catalysts and/or leveling agents. Examples of possible components are those described in Ullmann's Encyclopedia of Industrial Chemistry, $5^{th}$ Edition, Vol. A18, pp. 429-471, VCH, Weinheim 1991.

The coating compositions may be radiation-curable coating compositions. In this case, the binder essentially comprises monomeric or oligomeric compounds containing ethylenically unsaturated bonds, which after application are cured by actinic radiation, i.e. converted into a crosslinked, high molecular weight form. Where the system is UV-curing, it generally contains a photoinitiator as well. Suitable photoinitiators are well-known to the person skilled in the art and are preferably selected from halomethyloxadiazols, halomethyl-s-triazines, 3-aryl-substituted coumarins, benzophenones, acetophenones, cyclopentadiene-benzene-iron complexes, oxime esters and oximes.

The coating compositions can comprise an organic solvent or solvent mixture in which the binder is soluble. The coating composition can otherwise be an aqueous solution or dispersion. The vehicle can also be a mixture of organic solvent and water. The coating composition may be a high-solids paint or can be solvent-free (e.g. a powder coating material). Illustrative examples of solvent-free formulations are mixtures of acrylates or methacrylates, unsaturated polyester/styrene mixtures or mixtures of other ethylenically unsaturated monomers or oligomers. Powder coatings are, for example, those described in Ullmann's Encyclopedia of Industrial Chemistry, $5^{th}$ Edition, Vol. A18, pages 438-444. Powder coating materials may be in the form of a powder-slurry, too (dispersion of the powder preferably in water).

When used in a coating, the instant pigment preparations are incorporated into the coating as dispersed particles via techniques common in the art. The dispersion might be combined with the incorporation into the coating composition by use of adequate solvents.

The coating composition according to the invention may be applied to any desired substrate, for example, to metal, wood, plastic, composite, glass or ceramic material substrates by the customary methods, for example by dipping, knife application, film drawing, brushing, spraying, pouring, draw down, spin coating, dipping or electrophoresis, the coatings according to the invention being formed after drying and hardening, advantageously thermally or by irradiation.

For coloring coatings and printing inks, the high molecular weight organic materials and the pigment preparation according to the invention are finely dispersed or dissolved, optionally together with additives, such as stabilizers, dispersants, gloss improvers, fillers, other pigments, siccatives or plasticizers, generally in an organic and/or aqueous solvent or solvent mixture. It is possible to use a procedure in which the individual components are dispersed or dissolved separately or in which a plurality thereof are dispersed or dissolved together and only then all of the components combined.

When the high molecular weight material to be colored is a coating, it may be a customary coating or a specialty coating, for example, an automotive finish. The coating may be a constituent of a multi-layer finish. Effect finishes can be obtained by addition of metal flakes, uncoated or coated mica and/or interference pigments. The advantages of the pigment preparations according to the invention are particularly striking in coating applications.

Printing inks of generally known compositions are applied by customary methods, for example, by letterpress printing (flexographic printing), planographic printing (offset printing, lithographic printing), intaglio printing (rotogravure, steel engraving), screen printing or ink-jet printing (piezo or vapor bubble methods), for example to paper, card, metal, wood, leather, plastics or textiles, for publications, illustrations, packaging, banknotes, logistics documents or decoration. Further ink compositions can be used in ballpoint pens and felt-tip pens as well as in ink pads, ink ribbons and ink cartridges.

In addition, the pigment preparations of the invention are also suitable, for example, for the production of solid toners, wax transfer ribbons or, also preferred, color filters. Color filters customarily have red, blue and green pixels and also, in most cases, a black matrix on a transparent carrier material. Instant pigment preparations based on black organic pigments will generally be used in color filters to form the black matrix, while instant pigment preparations based on especially red, blue or green organic pigments, will generally be used in color filters to form one or more of the transparent layers, leading advantageously to surprisingly high transparency, high contrast, high color purity (chroma) and broader achievable color gamut.

The instant pigment preparations or compounds may also be used for the preparation of a color filter as well as to a color filter comprising image points (pixels) of at least three colors and optionally a black matrix, wherein a fraction of the image points and/or the optional black matrix comprise a pigment preparation of the invention. Accordingly, the invention relates to the use of the instant pigment preparations or compounds for the preparation of color filter as well as to a color filter comprising image points (pixels) of at least three colors and optionally a black matrix, wherein a fraction of the image points and/or the optional black matrix comprise a pigment preparation of the invention.

Color filters may usually comprise further, preferably colorless components which are customary in color filter formulations, such as solvents or, especially, additives, for example, stabilisers, antioxidants, UV absorbers, photostabilisers, wetting agents, surfactants, antifoams, plasticisers, texture-improvers, binders, dispersants and also, preferably, polymerisable monomers or oligomers, depolymerisable polymers and/or photoinitiators. Further components of that kind are added in a total amount of advantageously from 0 to 2000% by weight, based on the instant pigment preparations.

Compositions modifiable by radiation are also known as resists (for example, as described in WO 2007/113107). Radiation (for example, UV light) may, for example, be directed through a mask onto a coating of the composition, in the course of which the irradiated locations become either more insoluble or more soluble. Those parts of the layer which have remained soluble or become soluble are subsequently removed so that the desired image points remain behind. The latter are then usually thermally cured.

Any desired compositions modifiable by radiation can be used. Preference is given to compositions modifiable by radiation which are subsequently hardened optionally at a temperature of from 40 to 320° C., especially from 180 to 300° C., very especially from 200 to 250° C.

In another aspect, the invention relates to a coating prepared by curing a coating composition as defined above on a substrate.

Further, the instant compounds of formula (I) may be used as rheology modifiers, preferably for pigmented coating compositions. Most preferred are mid and especially high-solids coating compositions, usually such with a pigment:binder ratio of from about 1:1 to about 10:1 after curing. The light, weathering and heat stabilities are excellent, as are the negligible bleeding and the coating properties, such as, in particular, good rheology, high gloss, high tinctorial strength and excellent overcoating resistance.

Accordingly, in a further aspect the invention relates to the use of a compound of formula (I) as a rheology modifier.

Further, the instant compounds of formula (I) may be used as growth regulators, for example, during an after-treatment of a pigment such as recrystallization or grinding.

Accordingly, in a further aspect the invention relates to the use of a compound of formula (I) as a growth regulator.

A wide variety of organic modification of the pigment surface can be obtained by the disclosed process, applicable to the various uses of pigments. Only a one-step process of modification is required to perform, for example, in any liquid medium, such as water which is desired of environmental reasons. The binding of versatile organic functions to the pigment surface, attached directly or via a linker, opens many opportunities for further modification The pigment preparation of the invention exhibits improved rheology properties, above all, preparations having organic groups bearing polar groups. These organic groups may easily be attached to even pigments with a sterical hindrance. Further, said polar pigment surface of the inventive pigment preparation leads to increased interactions with polymeric dispersants, so-called hyperdispersants, for example, EFKA® 4046, 4047, 4060, 4300, 4330, 8512, Disperbyk® 161, 162, 163, 164, 165, 166, 168, 169, 170, 2000, 2001, 2050, 2090, 2091, 2095, 2096, 2105, 2150, PB® 711, 821, 822, 823, 824, 827, Solsperse® 24000, 31845, 32500, 32550, 32600, 33500, 34750, 36000, 36600, 37500, 39000, 41090, 44000, 53095, ALBRITECT® CP30 and combinations thereof as dispersant.

The pigment preparation of the invention shows improved dispersibility and dispersion stability, for example, by attaching groups of suitable polarity depending on the polarity of organic material to be colored. The polarity of the pigment preparation may easily be obtained by attaching suitable groups corresponding to the required application, for example, in mass-coloring depending on the kind of plastics. Long-chain substituents may easily be bound to preferably polar pigments. This was only possible by using long-chain substituted anilines or amino-naphthalines. Hydrophobic groups may also be of advantage in ink systems where often hydrophobic pigment preparations are required, for example, in toner systems made by emulsion polymerization for use in the electrophotography. Further, in paints, especially in high solids systems where hyperdispersants are often used, a higher polarity is desired. The surface modification of the pigment results especially in a reduction in the viscosity of the pigment dispersion, which enables the dispersion to be loaded with a greater amount of pigment.

The pigment preparation of the invention enables partially crystalline plastics to be mass-pigmented without warping, especially by imparting hydrophobic properties to pigments which contain polar groups per se.

The coloristic properties of the pigments are not adversely affected by said surface modification. The surface-modified pigment preparations are distinguished especially by very good fastness to light and to migration.

The following Examples illustrate the invention without limiting the scope thereof (% are by weight where not otherwise specified).

EXAMPLES

A) Radical Generators

Example 1

2,2'-azobis[2-methyl-N-(2-dodecanoyloxy ethyl)propionamide]

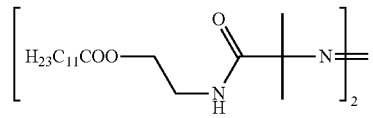

23.0 g (110 mmol) of lauryl chloride are slowly added to a solution of 14.4 g (50 mmol) of 2,2'-azobis[2-methyl-N-(2-hydroxyethyl)propionamide] (VA-086; Wako Pure Chemical Ind., Ltd) and 250 mg of 4-dimethylaminopyridine in 170 ml of dry pyridine at a temperature of 7-9° C. The solution is stirred at room temperature for 4 hours and then poured into 1500 ml of ice cold water. The precipitate is filtered off and recrystallized from acetonitrile/dichloromethane to obtain 28.7 g of 1 as a white powder (m.p. 69-72° C.).

$^1$H NMR (400 MHz, CDCl$_3$): 7.26 (m, NH), 4.23 (t, J=5.2 Hz, CH$_2$), 3.64 (m, CH$_2$), 2.30 (t, J=7.6 Hz, CH$_2$), 1.60 (m, CH$_2$), 1.35 (s, CH$_3$), 1.30 (m, CH$_2$), 0.88 (t, J=3.2 Hz, CH$_3$).

Example 2

2,2'-azobis[2-methyl-N-(2-octadecanoyloxy ethyl)propionamide]

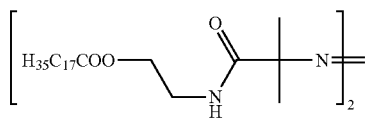

27.9 g (90 mmol) of stearyl chloride are slowly added to a solution of 11.5 g (40 mmol) of 2,2'-azobis[2-methyl-N-(2-hydroxyethyl)propionamide] (VA-086; Wako Pure Chemical Ind., Ltd) and 200 mg of 4-dimethylaminopyridine in 225 ml of dry pyridine at a temperature of 7-9° C. The solution is stirred at room temperature for 6 hours and then poured into 2200 ml of ice cold water. The precipitate is filtered off and recrystallized from ethyl acetate/dichloromethane to obtain 25.1 g of 2 as a white powder (m.p. 78-83° C.).

$^1$H NMR (400 MHz, CDCl$_3$): 7.26 (m, NH), 4.23 (t, J=5.2 Hz, CH$_2$), 3.65 (m, CH$_2$), 2.30 (t, J=7.6 Hz, CH$_2$), 1.61 (m, CH$_2$), 1.36 (s, CH$_3$), 1.26 (m, CH$_2$), 0.89 (t, J=3.2 Hz, CH$_3$).

Example 3

2,2'-azobis[2-methyl-N-(2-(pyridine-4-carbonyloxy) ethyl)propionamide]

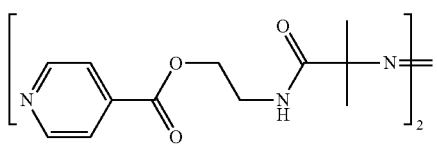

40.9 g (198 mmol) of dicyclohexyl carbodiimide are added to a suspension of 25.95 g (90 mmol) of 2,2'-azobis[2-methyl-N-(2-hydroxyethyl)propionamide] (VA-086; Wako Pure Chemical Ind., Ltd), 2.3 g of 4-dimethylaminopyridine and 24.38 g (198 mmol) of pyridine-4-carboxylic acid in 600 ml of dichloromethane. The mixture is stirred at room temperature for 18 hours, and the precipitate of dicyclohexylurea is filtered off. The filtrate is evaporated, and the residue is recrystallized twice from ethyl acetate to obtain 37.5 g of 3 as a white powder (m.p. 125-128° C.)

$^1$H NMR (400 MHz, CDCl$_3$): 7.75 (d, J=4.4 Hz, 2,6-H (Pyr)), 7.78 (d, J=4.4 Hz, 3,5-H(Pyr)), 7.24 (m, NH), 4.48 (t, J=5.6 Hz, CH$_2$,), 3.75 (m, CH$_2$), 1.26 (s, CH$_3$).

Example 4

2,2'-azobis[2-methyl-N-(2-((1-methylpyridin-1-ium-4-carbonyloxy)ethyl)propionamide]diiodide

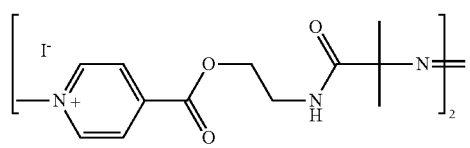

17.9 g (126 mmol) of methyl iodide are added to a suspension of 20.94 g (42 mmol) of 3 in 120 ml of acetonitrile. The mixture is stirred at room temperature for 100 hours in the dark. The orange crystalline precipitate is filtered off and dried in vacuum to obtain 32.65 g of 4 as an orange powder (m.p. 150-165° C.; decomposition).

$^1$H NMR (400 MHz, D$_2$O): 8.97 (d, J=6.8 Hz, 2,6-H(Pyr)), 8.45 (d, J=4.4 Hz, 3,5-H(Pyr)), 4.54 (t, J=5.2 Hz, CH$_2$,), 4.43 (s, CH$_3$), 3.71 (m, CH$_2$), 1.21 (s, CH$_3$).

B) Modification of Pigment Surfaces

Example 101

20 g of C.I. Pigment Red 264 (Irgazin DPP Rubin TR) are dispersed in 300 ml of water using a high-speed stirrer (IKA-Ultra-Turrax® T45) and subsequently an impeller to form a pigment slurry. A solution of 1.2 g of 2,2'-Azobis[N-(2-carboxyethyl)-2-methylpropionamidine]hydrate (VA-057; Wako Pure Chemical Ind., Ltd.) in 100 ml of water is added with stirring, followed by adjusting the pH at 3.5 with diluted HCl. The slurry is heated to 90° C. for 3 hours. After cooling to room temperature the product is isolated by filtration and dried at 80° C. under vacuum. A MALDI-TOF mass spectrum of the final product indicates the presence of the substituted chromophore by a peak at 595 m/z. The starting material has no corresponding peaks at this mass to charge ratios.

Example 102

Example 101 is repeated except that 20 g of C.I. Pigment Red 254 (Irgazin Red 2030) are used instead of C.I. Pigment Red 264.

Example 103

Example 101 is repeated except that 20 g of C.I. Pigment Blue 15.1 (Heliogen Blue L6950) are used instead of C.I. Pigment Red 264.

Example 104

20 g of C.I. Pigment Red 254 (Irgazin Red 2030) are dispersed in 200 ml of water using a high-speed stirrer (IKA-Ultra-Turrax® T45) and subsequently an impeller to form a pigment slurry. A solution of 1.2 g of 2,2'-azobis[2-methyl-N-(2-hydroxyethyl)propionamide] (VA-086; Wako Pure Chemical Industries, Ltd.) in 100 ml of water is added with stirring followed by adjusting the pH at 3.5 with diluted HCl. The slurry is heated to reflux for 24 hours. After cooling to room temperature the product is isolated by filtration and dried at 80° C. under vacuum.

A MALDI-TOF mass spectrum of the final product indicates the presence of the substituted chromophore by a peak at 487 m/z. The starting material has no corresponding peaks at this mass to charge ratios.

Example 105

Example 104 is repeated except that 20 g of C.I. Pigment Blue 15.1 are used instead of C.I. Pigment Red 254.

Example 106

13 g of C.I. Pigment Red 264 (Irgazin DPP Rubin TR) are dispersed in 300 ml of water using a high-speed stirrer (IKA-Ultra-Turrax® T45) and subsequently an impeller to form a pigment slurry. A solution of 0.6 g of 2,2'-azobis(N,N'-dimethyleneisobutyramidine) hydrochloride (VA-044; Wako Pure Chemical Ind., Ltd.) in 100 ml of water is added with stirring. The slurry is heated to 80° C. for 2 hours. After cooling to room temperature the product is isolated by filtration and dried at 80° C. under vacuum.

A MALDI-TOF mass spectrum of the final product indicates the presence of the substituted chromophore by a peak at 549 m/z. The starting material has no corresponding peaks at this mass to charge ratios.

Example 107

10 g of C.I. Pigment Blue 15.3 (Cromophtal Blue 4GNP) are dispersed in 150 g of 2-propanol. After adding 2 g of the radical generator prepared in Example 1 the slurry is heated at reflux for 30 hours. After cooling the product is recovered by filtration, washed with 2-propanol followed by water and dried at 60° C. in a vacuum oven.

Example 108

Example 107 is repeated except that the radical generator prepared in Example 2 is used instead the radical generator prepared in Example 1.

Example 109

46 g of a 21.8% filter cake of C.I. Pigment Red 202 (corresponding to 10 g of pigment) are dispersed in 150 g of water. After adding 2 g of the radical generator prepared in Example 3 the slurry is heated at reflux for 27 hours. Then, the product is recovered by filtration, washed with water and dried at 60° C. in a vacuum oven.

Example 110

Example 109 is repeated except that the radical generator prepared in Example 4 is used instead the radical generator prepared in Example 3.

C) Application Examples

Examples 201 and 202

Warpage Behaviour

Example 201

0.7 g of the dried product of Example 107 and 700 g of a polymer (HDPE Sabic M80063S Powder) are dry-mixed in a tumble mixer for 10 minutes. The mixture is extruded twice in a double screw extruder at 200° C. The resulting pellets are processed on an injection molding machine at 240° C. to give panels measuring 100×100×2 mm. Then, the panels are thermally conditioned in a water-bath at 90° C. for 30 minutes and stored at room temperature (23° C.) for at least 15 hours. The panels are measured precisely following DIN EN ISO 294-4:2003.

The dimension stability of the obtained panels is distinctly better than of a reference which is a non-modified C.I. Pigment Blue 15:3.

Example 202

Example 201 is repeated except that the product of Example 108 is used instead of the product of Example 107.

The dimension stability of the obtained panels is better than of the reference.

Examples 203 and 204

Preparation of a Low-Solids CAB-PES-Paint

Example 203 a) 7.50 g of the pigment prepared in Example 109,
b) 98.90 g of a CAB solution consisting of:
41.00 g of cellulose acetobutyrate CAB-531-1 (20% in butanol/xylene 2:1 (Eastman Chem.))
1.50 g of zirconium octoate,
18.50 g of Solvesso® 150 (aromatic solvent, ExxonMobil Chemicals),
21.50 g of butyl acetate, and
17.50 g of xylene;
c) 36.50 g of polyester resin DYNAPOL® H700 (Dynamit Nobel),
d) 4.60 g of melamine resin MAPRENAL® MF650 (Hoechst), and
e) 2.50 g of dispersant DISPERBYK® 160 (BykChemie).

Components a) to e) are dispersed together for 90 minutes using a shaker machine (total coating material: 150 g; 5% pigment).

For the base-coat formulation, 26.67 g of the resulting masstone lacquer are mixed with 17.31 g of Al stock solution (8%) consisting of
12.65 g SILBERLINE® SS 3334AR, 60% (Silberline Ltd),
56.33 g of CAB solution (composition as above),
20.81 g of polyester resin DYNAPOL H700,
2.60 g of melamine resin MAPRENAL MF650, and
7.59 g of Solvesso 150,
and applied by spraying onto an aluminium panel (wet film about 20 μm). After evaporation for 30 minutes at room temperature, a thermosetting acrylic varnish consisting of
29.60 g of acrylic resin URACRON® 2263 XB, 50% in xylene/butanol (Chem Fabr. Schweizer-halle),
5.80 g of melamine resin CYMEL® 327, 90% in isobutanol,
2.75 g of butyl glycol acetate,
5.70 g of xylene,
1.65 g of n-butanol,
0.50 g of silicone fluid, 1% in xylene,
3.00 g of light stabilizer TINUVIN® 900, 10% in xylene (BASF), and
1.00 g of light stabilizer TINUVIN 292, 10% in xylene (BASF),
is applied by spraying as top-coat formulation (wet film about 50 μm). After drying in air for further 30 minutes at room temperature, the formulation is baked at 130° C. for 30 minutes. A red-magenta coating with very good resistance properties is obtained.

Example 204

Example 203 is repeated except that the product of Example 110 is used instead of the product of Example 109. A red-magenta coating with very good resistance properties is obtained.

Examples 205 and 206

Preparation of a High-Solids Solventborne Pigment Paste

Example 205

The pigment preparation of Example 109 is tested in the high solids system described below.

A continuous phase is prepared by mixing a combination of
a) 55 weight parts of an aromatic naphtha-based solvent (Solvesso 100, ExxonMobil Chemicals),
b) 28 weight parts of a high-solids acrylic resin (Joncryl® 902, BASF), and
c) 5 weight parts of a pigment dispersant (Efka® 4310, BASF) by stirring (500-800 rpm) using a disperser equipped with a Cowles blade (toothed blade). Once homogeneous, 12 weight parts of Example 109 (modified C.I. Pigment Red 202) are added under stirring thereto.

The slurry is pre-dispersed using the same disperser/Cowles blade combination mentioned above for 30 minutes at 2000 rpm to ensure large pigment agglomerates are adequately 'wetted-out' in the continuous phase. The 'wetted-out' slurry is transferred to a re-circulation dispersion mill filled with zirconia grinding media and then dispersed, wherein the temperature of the mill charge is maintained ≤60° C. by using cooling water. The dispersion is continued until the maximum particle size of the dispersed pigment is ≤5 µm according to a Hegmann grind gauge. Once dispersion is achieved, the contents of the mill are charged into a suitable re-sealable container.

The above millbase has a total solids content of 33.5%, a ratio of pigment:binder of 1:2 and a pigment content of 12%.

The rheological behaviour of the millbase is measured with a Haake cone/plate equipment at 23° C.

A 'let-down' clear is prepared: 40 weight parts of an acrylic binder (Joncryl 500, BASF) and 30 weight parts of a solvent mixture (1:1 n-butyl acetate:xylene) are stirred together using a conventional propeller stirrer blade attached to an overhead stirrer unit. 17.5 weight parts of a melamine formaldehyde binder (Luwipal® 066 LF, BASF) are added at a controlled rate under stirring. Separately, a mixture of 1.5 weight parts of an amine neutralized dodecylbenzenesulfonic acid (DDBSA) catalyst (Nacure® 5225, King Industries) and 11 weight parts of a solvent mixture (1:1 n-butyl acetate:xylene) is prepared under stirring. Once homogenised, the mixture is added to the stirred binder mixture. Stirring is continued for further 30 minutes to ensure all components are homogeneously mixed.

50 weight parts of pigmented millbase are added under stirring to 50 weight parts of the 'let-down' clear.

The resulting paint has a total solids content of 42%, a ratio of pigment:binder of 1:6 and a pigment content of 6%.

The homogeneous paint can be adjusted to viscosity using a 1:1 mixture of n-butylacetate:xylene and adjusted to a spray viscosity of 17 secs in a DIN 4 flow cup. Spray application is performed by use of a HVLP spray gun (SATA 90 or SATA Jet RP).

The rheology of the millbase (before let-down) is measured, and delivered strong improvement against the reference (a millbase comprising non-surface-modified C.I. Pigment Red 202).

Example 206

Example 205 is repeated except that the product of Example 110 is used instead of the product of Example 109.

The rheology of the millbase (before let-down) is measured, and delivered strong improvement against the reference (a millbase comprising non-surface-modified C.I. Pigment Red 202).

The invention claimed is:

1. A pigment composition, comprising:
(a) an organic pigment comprising a chromophore $Q^1$; and
(b) from 0.1 to 30 mol, based on 100 mol of the organic pigment (a), of a compound of formula (I):

$$[Q^2 \!\!-\!\! \begin{array}{c} R^1 \\ | \\ | \\ R^2 \end{array} \!\!-\!\! R^3]_m,$$ (I)

wherein $Q^2$ is an m-valent residue of the chromophore $Q^1$;
$R^1$ and $R^2$ are each independently CN, $C_1$-$C_6$alkyl, $C_3$-$C_7$cycloalkyl, or $C_6$-$C_{18}$aryl, wherein an alkyl group of the $C_1$-$C_6$alkyl or a cycloalkyl group of the $C_3$-$C_7$cycloalkyl is optionally substituted with D and an aryl group of the $C_6$-$C_{18}$aryl is optionally substituted with E; or
$R^1$ and $R^2$ together with a linking carbon atom form a 5 to 12 membered ring, wherein the 5 to 12 membered ring is optionally substituted with E and the 5 to 12 membered ring optionally further comprises at least one selected from the group consisting of —O—, —$NR^4$—, —N(—$OR^4$)—, and —$N^+R^4R^5$ $An^-$-;
$R^3$ is $C_1$-$C_{25}$alkyl, $C_3$-$C_{25}$alkenyl, $C_7$-$C_{25}$aralkyl, or a group of formula (II):

$$-\!\!-\!\!\!\!\!\text{\Large[}\!X\!\text{\Large]}_p\!\text{\Large[}\!Y\!\text{\Large]}_q\!\!-\!\!Z,$$ (II)

wherein an alkyl group of the $C_1$-$C_{25}$alkyl or an alkenyl group of the $C_3$-$C_{25}$alkenyl is optionally substituted with D and an aryl group of the $C_7$-$C_{25}$aralkyl is optionally substituted with E;
p and q are each independently 0 or 1;
X is —O—, —S—, —$NR^6$—, —$CONR^6$—, —COO—, or —C(=$NR^7$)$NR^8$—;
Y is $C_1$-$C_{25}$alkylene, wherein an alkylene group of the $C_1$-$C_{25}$alkylene optionally comprises, at an end or within a chain, at least one selected from the group consisting of —O—, —S—, —CO—, —COO—, —$CONR^6$—, —$NR^6$—, —$N^+R^6R^5$ $An^-$-, an alicyclic ring, and an aromatic ring, and an alkylene group of the $C_1$-$C_{25}$alkylene is optionally substituted one or more times with Z;
Z is H; $OR^9$ $OCOR^9$; CN; $NR^9R^{10}$; $N^+R^9R^{10}R^5$ $An^-$; $C_6$-$C_{18}$aryl; or a heterocyclic $C_2$-$C_{20}$ ring system wherein an aryl group of the $C_6$-$C_{18}$aryl is optionally substituted with E; $COOR^9$; $CONR^9R^{10}$;

$$\begin{array}{c} NR^{11} \\ \parallel \\ NR^{12}R^{13} \end{array};$$

$SO_2R^9$; $SO_3R^9$; $SO_2NR^9R^{10}$; $SO_3^-Cat^+$; or $PO(OR^9)_2$, the heterocyclic $C_2$-$C_{20}$ ring system comprises at least one selected from the group consisting of O, S, N, $NR^4$, $NOR^4$, $N^+R^4R^5\,An^-$, and $N^+R^5\,An^-$, and the heterocyclic $C_2$-$C_{20}$ ring system is optionally substituted with E;

- $R^4$ is H or $C_1$-$C_4$alkyl, wherein an alkyl group of the $C_1$-$C_4$alkyl is optionally substituted with D;
- $R^5$ is H, $C_1$-$C_4$alkyl, $C_7$-$C_{10}$aralkyl, or $C_3$-$C_5$alkenyl;
- $R^6$, $R^7$, $R^8$, $R^9$, $R^{10}$, $R^{11}$, $R^{12}$, and $R^{13}$ are each independently H, $C_1$-$C_{18}$alkyl, $C_3$-$C_{18}$alkenyl, $C_5$-$C_{12}$cycloalkyl, $C_6$-$C_{18}$aryl, or $C_7$-$C_{18}$aralkyl, wherein an alkyl group of the $C_1$-$C_{18}$alkyl, an alkenyl group of the $C_3$-$C_{18}$alkenyl, or a cycloalkyl group of the $C_5$-$C_{12}$cycloalkyl is optionally substituted with D;

and an aryl group of the $C_6$-$C_{18}$aryl or the $C_7$-$C_{18}$aralkyl is optionally substituted with E; or

- $R^9$ and $R^{10}$ together with a linking nitrogen atom form a 5 to 7 membered heterocyclic ring, wherein the 5 to 7 membered heterocyclic ring is optionally substituted with E, and the 5 to 7 membered heterocyclic ring optionally further comprises at least one selected from the group consisting of —O—, —$NR^4$—, and —$N^+R^4R^5\,An^-$—; or
- $R^{12}$ and $R^{13}$ together with a linking nitrogen atom form a 5 to 7 membered heterocyclic ring, wherein the 5 to 7 membered heterocyclic ring is optionally substituted with E, and the 5 to 7 membered heterocyclic ring optionally further comprises at least one selected from the group consisting of O, N, $NR^4$, $N^+R^4R^5\,An^-$, and $N^+R^5\,An^-$; or
- $R^{11}$ and $R^{12}$ together with a linking NCN group form a 5 to 7 membered cyclic amidine, wherein an amidine group of the 5 to 7 membered cyclic amidine is optionally substituted with E;

E is $C_1$-$C_4$alkyl, $C_1$-$C_4$alkoxy, COOH, OH, halogen, $NR^9R^{10}$, —$N^+R^9R^{10}R^5\,An^-$, $SO_3R^9$, $SO_2NR^9R^{10}$, or $SO_3^-Cat^+$;

D is $C_1$-$C_4$alkoxy, OH, COOH, or halogen;

$An^-$ is an equivalent of an anion;

$Cat^+$ is an equivalent of a cation;

m is an integer from 1 to 4; and each group of formula (III):

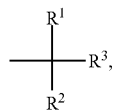

(III)

is selected independently.

2. The pigment composition according to claim 1, wherein the organic pigment is at least one pigment selected from the group consisting of bis(anthraquinone-1-yl-amino), bis(anthraquinone-1-yl-oxy), 1,1'-dianthraquinolyl, diketopyrrolopyrrole, indanthrone, isoindoline, isoindolinone, perylene, 1-phenylhydrazono-2-oxy-3-carbamoyl-1,2-dihydronaphthalene, phthalocyanine, and a quinacridone pigment, or a mixture of said pigments, including a solid solution or a mixed crystal.

3. The pigment composition according to claim 1, wherein m is 1 or 2.

4. The pigment composition according to claim 1, wherein $R^1$ and $R^2$ are each independently $C_1$-$C_6$alkyl, or $R^1$ and $R^2$ together with a linking carbon atom form a 5 to 12 membered ring, wherein the 5 to 12 membered ring is optionally substituted with E and the 5 to 12 membered ring optionally further comprises at least one selected from the group consisting of —O—, —$NR^4$—, —N(—$OR^4$)—, and —$N^+R^4R^5\,An^-$—;

$R^3$ is a group of formula (II):

(II)

p and q are 0,

Z is $OR^9$, $OCOR^9$; CN; $NR^9R^{10}$, $N^+R^9R^{10}R^5\,An^-$; $C_6$-$C_{18}$aryl, or a heterocyclic $C_2$-$C_{20}$ ring system wherein an aryl group of the $C_6$-$C_{18}$aryl is optionally substituted with E; $COOR^9$; $CONR^9R^{10}$;

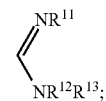

$SO_2R^9$; $SO_3R^9$; $SO_2NR^9R^{10}$, $SO_3^-Cat^+$;

or $PO(OR^9)_2$; the heterocyclic $C_2$-$C_{20}$ ring system comprises at least one selected from the group consisting of O, S, N, $NR^4$, $NOR^4$, $N^+R^4R^5\,An$ and $N^+N^5\,An^-$, and the heterocyclic $C_2$-$C_{20}$ ring system is optionally substituted with E;

$R^9$, $R^{10}$, $R^{11}$, $R^{12}$, and $R^{13}$ are each independently H, $C_1$-$C_{18}$alkyl, $C_3$-$C_8$alkenyl, $C_5$-$C_7$cycloalkyl, $C_6$-$C_{18}$aryl, and $C_7$-$C_{18}$aralkyl, wherein an alkyl group of the $C_1$-$C_{18}$alkyl, an alkenyl group of the $C_3$-$C_8$alkenyl or a cycloalkyl group of the $C_5$-$C_7$cycloalkyl is unsubstituted or optionally substituted with D;

and the aryl group of the $C_6$-$C_{18}$aryl or the $C_7$-$C_{18}$aralkyl is optionally substituted with E; or

- $R^9$ and $R^{10}$ together with a linking nitrogen atom form a 5 or 6 membered heterocyclic ring, wherein the 5 or 6 membered heterocyclic ring is optionally substituted with E, and the 5 or 6 membered heterocyclic ring optionally further comprises at least one selected from the group consisting of —O—, —$NR^4$— and —$N^+R^4R^5\,An^-$—; or
- $R^{12}$ and $R^{13}$ together with a linking nitrogen atom form a 5 or 6 membered heterocyclic ring, wherein the 5 or 6 membered heterocyclic ring is optionally substituted with E, and the 5 or 6 membered heterocyclic ring optionally further comprises at least one selected from the group consisting of O, N, $NR^4$, $N^+R^4R^5\,An^-$, and $N^+R^5\,An^-$; or
- $R^{11}$ and $R^{12}$ together with a linking NCN group form a 5 to 6 membered cyclic amidine, wherein an amidine group of the 5 to 6 membered cyclic amidine is optionally substituted with E.

5. The pigment composition according to claim 1, wherein $R^1$ and $R^2$ are each independently $C_1$-$C_6$alkyl or CN;

$R^3$ is a group of formula (II):

(II)

p and q are each independently 0 or 1, wherein a sum of p and q is 1 or 2;

X is —O—, —S—, —$NR^6$—, —$CONR^6$—, —COO—, or —C(=$NR^7$)$NR^8$—;

Y is $C_1$-$C_{25}$alkylene, wherein an alkylene group of the $C_1$-$C_{25}$alkylene optionally comprises at an end or within a chain, at least one selected from the group consisting of —O—, —S—, —CO—, —COO—, —$CONR^6$—, —NR$^6$—, —N$^+$R$^6$R$^5$ An$^-$—, cyclohexylene, phenylene, and naphthylene, and an alkylene group of the C$_1$-C$_{25}$alkylene is optionally substituted one or more times with Z;

Z is H; OR$^9$ OCOR$^9$; CN; NR$^9$R$^{10}$, —N$^+$R$^9$R$^{10}$R$^5$ An$^-$; C$_6$-C$_{18}$aryl, or an optionally saturated heterocyclic C$_2$-C$_{20}$ring system, wherein an aryl group of the C$_6$-C$_{18}$aryl is optionally substituted with E; COOR$^9$; CONR$^9$R$^{10}$;

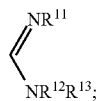

SO$_2$R$^9$; SO$_3$R$^9$; SO$_2$NR$^9$R$^{10}$, SO$_3$$^-$Cat$^+$; or PO(OR$^9$)$_2$, the optionally saturated heterocyclic C$_2$-C$_{20}$ring system comprises at least one selected from the group consisting of O, S, N, NR$^4$, NOR$^4$, N$^+$R$^4$R$^5$ An$^-$, and N$^+$R$^5$ An$^-$, and the optionally saturated heterocyclic C$_2$-C$_{20}$ring system is optionally substituted with E;

R$^6$, R$^7$, R$^8$, R$^9$, R$^{10}$, R$^{11}$, R$^{12}$, and R$^{13}$ are each independently H, C$_1$-C$_{18}$alkyl, C$_3$-C$_8$alkenyl, C$_5$-C$_7$cycloalkyl, C$_6$-C$_{18}$aryl, or C$_7$-C$_{18}$aralkyl wherein an alkyl group of the C$_1$-C$_{18}$alkyl, an alkenyl group of the C$_3$-C$_8$alkenyl, or a cycloalkyl group of the C$_5$-C$_7$cycloalkyl is optionally substituted with D, and an aryl group of the C$_6$-C$_{18}$aryl or the C$_7$-C$_{18}$aralkyl is optionally substituted with E; or R$^9$ and R$^{10}$, or R$^{12}$, and R$^{13}$ together with a linking nitrogen atom form a 5 or 6 membered heterocyclic ring, wherein the 5 or 6 membered heterocyclic ring is optionally substituted with E, and the 5 or 6 membered heterocyclic ring optionally further comprises —O—, —NR$^4$—, or —N$^+$R$^4$R$^5$ An$^-$; or R$^{11}$ and R$^{12}$ together with a linking NCN group form a 5 or 6 membered cyclic amidine, wherein an amidine group of the 5 or 6 membered cyclic amidine is optionally substituted with E.

6. The pigment composition according to claim 5, wherein R$^1$ and R$^2$ are each independently methyl or ethyl, R$^3$ is a group of formula (II):

p is 1, and q is 1;
X is —CONR$^6$—, —COO—, or —C(=NR$^7$)NR$^8$—;
Y is C$_1$-C$_6$alkylene;
Z is OR$^9$, OCOR$^9$; NR$^9$R$^{10}$; or —N$^+$R$^9$R$^{10}$R$^5$ An$^-$;
R$^6$, R$^7$, R$^8$, R$^9$, and R$^{10}$ are each independently H, C$_1$-C$_{18}$alkyl, C$_3$-C$_8$alkenyl, C$_5$-C$_7$cycloalkyl, C$_6$-C$_{18}$aryl, or C$_7$-C$_{18}$aralkyl, wherein an alkyl group of the C$_1$-C$_{18}$alkyl, an alkenyl group of the C$_3$-C$_8$alkenyl or the cycloalkyl group of the C$_5$-C$_7$cycloalkyl is optionally substituted with D, and an aryl group of the C$_6$-C$_{18}$aryl or the C$_7$-C$_{18}$aralkyl is optionally substituted with E; or R$^9$ and R$^{10}$ together with a linking nitrogen atom form a 5 or 6 membered heterocyclic ring, wherein the 5 or 6 membered ring is optionally substituted with E, and the 5 or 6 membered ring optionally further comprises —O—, —NR$^4$—, or —N$^+$R$^4$R$^5$ An$^-$.

7. The pigment composition according to claim 5, wherein R$^1$ and R$^2$ are methyl or ethyl
R$^3$ is a group of formula (II):

p is 1 and q is 1;
X is —CONR$^6$—, —COO—, or —C(=NR$^7$)NR$^8$—;
Y is C$_1$-C$_{25}$alkylene, wherein an alkylene group of the C$_1$-C$_{25}$alkylene optionally comprises at an end or within a chain, at least one selected from the group consisting of —O—, —CO—, —COO—, —CONR$^6$—, —NR$^6$—, and —N$^+$R$^6$R$^5$ An$^-$;
Z is phenyl, naphthyl, or a saturated heterocyclic C$_2$-C$_{20}$ring system or C$_2$-C$_{18}$hetaryl ring system, wherein the phenyl or the naphthyl is optionally substituted with E, the saturated heterocyclic C$_2$-C$_{20}$ring system or C$_2$-C$_{18}$hetaryl ring system comprises at least one selected from the group consisting of O, S, N, NR$^4$, NOR$^4$, N$^+$R$^4$R$^5$ An$^-$ and N$^+$R$^5$ An$^-$, and the saturated heterocyclic C$_2$-C$_{20}$ring system or C$_2$-C$_{18}$hetaryl ring system is optionally substituted with E;
R$^6$, R$^7$, and R$^8$ are each independently H or C$_1$-C$_{18}$alkyl.

8. The pigment composition according to claim 1, wherein R$^1$ and R$^2$ are each independently C$_1$-C$_6$alkyl, or
R$^1$ and R$^2$ together with a linking carbon atom form a 5 to 12 membered alicyclic ring, wherein the 5 to 12 membered alicyclic ring is optionally substituted with E;
R$^3$ is C$_1$-C$_{25}$alkyl, C$_3$-C$_{25}$alkenyl, or C$_7$-C$_{25}$aralkyl, wherein an alkyl group of the C$_1$-C$_{25}$alkyl or an alkenyl group of the C$_3$-C$_{25}$alkenyl is optionally substituted with D, and an aryl group of the C$_7$-C$_{25}$aralkyl is optionally substituted with E, and
D and E are each independently C$_1$-C$_4$alkyl.

9. A compound of formula (I):

wherein Q$^2$ is an m-valent residue of a chromophore Q$^1$ of at least one organic pigment selected from the group consisting of bis(anthraquinone-1-yl-amino), bis(anthraquinone-1-yl-oxy), 1,1'-dianthraquinolyl, diketopyrrolopyrrole, indanthrone, isoindoline, isoindolinone, perylene, 1-phenylhydrazono-2-oxy-3-carbamoyl-1,2-dihydronaphthalene, and a quinacridone pigment, including a solid solution or a mixed crystal;
R$^1$ and R$^2$ are each independently CN, C$_1$-C$_6$alkyl, C$_3$-C$_7$cycloalkyl, and C$_6$-C$_{18}$aryl, wherein an alkyl group of the C$_1$-C$_6$alkyl or a cycloalkyl group of the C$_3$-C$_7$cycloalkyl is optionally substituted with D, and an aryl group of the C$_6$-C$_{18}$aryl is optionally substituted with E; or
R$^1$ and R$^2$ together with a linking carbon atom form a 5 to 12 membered ring, wherein the 5 to 12 membered ring is optionally substituted with E, and the 5 to 12 membered ring optionally further comprises at least one selected from the group consisting of —O—, —NR$^4$—, —N(—OR$^4$)—, and —N$^+$R$^4$R$^5$ An$^-$;

$R^3$ is $C_1$-$C_{25}$alkyl, $C_3$-$C_{25}$alkenyl, $C_7$-$C_{25}$aralkyl, or a group of formula (II):

$$-\!\!\left[\mathrm{X}\right]_{\overline{p}}\!\!\left[\mathrm{Y}\right]_{\overline{q}}\!\!-\!\mathrm{Z}, \qquad (\mathrm{II})$$

wherein an alkyl group of the $C_1$-$C_{25}$alkyl or an alkenyl group of the $C_3$-$C_{25}$alkenyl is optionally substituted with D, an aryl group of the $C_7$-$C_{25}$aralkyl is optionally substituted with E, p and q are each independently 0 or 1;

X is —O—, —S—, —NR$^6$—, —CONR$^6$—, —COO—, or —C(=NR$^7$)NR$^8$—;

Y is $C_1$-$C_{25}$alkylene, wherein an alkylene group of the $C_1$-$C_{25}$alkylene optionally comprises at an end or within a chain, at least one selected from the group consisting of —O—, —S—, —CO—, —COO—, —CONR$^6$—, —NR$^6$—, —N$^+$R$^6$R$^5$ An$^-$, an alicyclic ring, and an aromatic ring, and the alkylene group is optionally substituted one or more times with Z;

Z is H; OR$^9$; OCOR$^9$; CN; NR$^9$R$^{10}$; N$^+$R$^9$R$^{10}$R$^5$ An$^-$; $C_6$-$C_{18}$aryl; or a heterocyclic $C_2$-$C_{20}$ring system, wherein an aryl group of the $C_6$-$C_{18}$aryl is optionally substituted with E; COOR$^9$; CONR$^9$R$^{10}$;

[structure showing =C(NR$^{11}$)(NR$^{12}$R$^{13}$)]

SO$_2$R$^9$; SO$_3$R$^9$; SO$_2$NR$^9$R$^{10}$ SO$_3^-$Cat$^+$; or PO(OR$^9$)$_2$; wherein the heterocyclic $C_2$-$C_{20}$ring system comprises at least one selected from the group consisting of O, S, N, NR$^4$, NOR$^4$, N$^+$R$^4$R$^5$ An$^-$, and N$^+$R$^5$ An$^-$, the heterocyclic $C_2$-$C_{20}$ring system is optionally substituted with E;

R$^4$ is H or $C_1$-$C_4$alkyl, wherein an alkyl group of the $C_1$-$C_4$alkyl is optionally substituted with D;

R$^5$ is H, $C_1$-$C_4$alkyl, $C_7$-$C_{10}$aralkyl, or $C_3$-$C_5$alkenyl;

R$^6$, R$^7$, R$^8$, R$^9$, R$^{10}$, R$^{11}$, R$^{12}$, and R$^{13}$ are each independently H, $C_1$-$C_{18}$alkyl, $C_3$-$C_{18}$alkenyl, $C_5$-$C_{12}$cycloalkyl, $C_6$-$C_{18}$aryl, or $C_7$-$C_{18}$aralkyl wherein an alkyl group of the $C_1$-$C_{18}$alkyl, an alkenyl group of the $C_3$-$C_{18}$alkenyl, or a cycloalkyl group of the $C_5$-$C_{12}$cycloalkyl is optionally substituted with D;

and an aryl group of the $C_6$-$C_{18}$aryl or the $C_7$-$C_{18}$aralkyl is optionally substituted with E; or R$^9$ and R$^{10}$ together with a linking nitrogen atom form a 5 to 7 membered heterocyclic ring, wherein the 5 to 7 membered heterocyclic ring is optionally substituted with E, and wherein the 5 to 7 membered heterocyclic ring optionally further comprises at least one selected from the group consisting of —O—, —NR$^4$—, and —N$^+$R$^4$R$^5$ An$^-$-; or R$^{12}$ and R$^{13}$ together with a linking nitrogen atom form a 5 to 7 membered heterocyclic ring, wherein the 5 to 7 membered heterocyclic ring is optionally substituted with E, and the 5 to 7 membered heterocyclic ring optionally further comprises at least one selected from the group consisting of O, N, NR$^4$, N$^+$R$^4$R$^5$ An$^-$, and N$^+$R$^5$ An$^-$; or R$^{11}$ and R$^{12}$ together with a linking NCN group form a 5 to 7 membered cyclic amidine, wherein an amidine group of the 5 to 7 membered cyclic amidine is optionally substituted with E;

E is $C_1$-$C_4$alkyl, $C_1$-$C_4$alkoxy, COOH, OH, halogen, NR$^9$R$^{10}$, —N$^+$R$^9$R$^{10}$R$^5$ An$^-$, SO$_3$R$^9$, SO$_2$NR$^9$R$^{10}$, or SO$_3^-$Cat$^+$;

D is $C_1$-$C_4$alkoxy, OH, COOH, or halogen;

An$^-$ is an equivalent of an anion;

Cat$^+$ is an equivalent of a cation;

m is an integer from 1 to 4; and each group of formula (III):

$$\begin{array}{c} R^1 \\ | \\ -\!\!\!-\!\!\!-R^3, \\ | \\ R^2 \end{array} \qquad (\mathrm{III})$$

is selected independently.

10. A process for preparing the pigment composition of claim 1, the process comprising:
treating a suspension of the organic pigment with a radical of formula (IV):

$$\begin{array}{c} R^1 \\ | \\ R^3-\!\!\!\overset{\bullet}{C}\!\!\!- \\ | \\ R^2 \end{array} \qquad (\mathrm{IV})$$

11. An azo compound of formula (V):

$$[R^3\!\!\!-\!\!\!\overset{\overset{R^1}{|}}{\underset{\underset{R^2}{|}}{\phantom{C}}}\!\!\!-\!\!\!N\!\!\equiv\!\!\!N]_{\overline{2}}, \text{ or} \qquad (\mathrm{V})$$

formula (VI):

$$R^3\!\!\!-\!\!\!\overset{\overset{R^1}{|}}{\underset{\underset{R^2}{|}}{\phantom{C}}}\!\!\!-\!\!\!N\!\!=\!\!N\!\!-\!\!R^{14}, \qquad (\mathrm{VI})$$

wherein

R$^1$ and R$^2$ together with a linking carbon atom form a 8 to 12 membered ring or a 5 to 7 membered ring wherein the 8 to 12 membered ring or the 5 to 7 membered ring is optionally substituted with E, and the 5 to 7 membered ring comprises one or more groups of —N(—OR$^4$)—;

R$^3$ is CN; and

R$^{14}$ is phenyl, triphenylmethyl, or CONR$^{15}$R$^{16}$, wherein R$^{15}$ and R$^{16}$ are each independently H, $C_1$-$C_4$alkyl, —

[structure: CH$_2$CH$_2$—N(H)—C(=O)—N=N—C(R$^1$)(R$^2$)—R$^3$]

or
the azo compound of formula (V), wherein $R^1$ and $R^2$ are each independently CN, $C_1$-$C_6$alkyl, $C_3$-$C_7$cycloalkyl, or $C_6$-$C_{18}$aryl, wherein an alkyl group of the $C_1$-$C_6$alkyl or a cycloalkyl group of the $C_3$-$C_7$cycloalkyl is optionally substituted with D, and an aryl group of the $C_6$-$C_{18}$aryl, is optionally substituted with E;

$R^3$ is a group of formula (II):

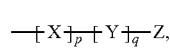   (II)

p and q are each independently 0 or 1;

X is —$CONR^6$—, —COO—, or —$C(=NR^7)NR^8$—;

Y is $C_1$-$C_{25}$alkylene, wherein an alkylene group of the $C_1$-$C_{25}$alkylene optionally comprises at an end or within a chain, at least one group selected from the group consisting of —O—, —S—, —CO—, —COO—, —$CONR^6$—, —$NR^6$—, —$N^+R^6R^5$ $An^-$-, an alicyclic ring, and an aromatic ring, wherein the alkylene group is optionally substituted one or more times with Z;

Z is $SO_2R^9$; $SO_3R^9$; $SO_2NR^9R^{10}$, $SO_3^-$ $Cat^+$; $PO(OR^9)_2$; a saturated heterocyclic $C_2$-$C_{20}$ring system; or $C_2$-$C_{18}$heteroaryl, wherein the saturated heterocyclic $C_2$-$C_{20}$ring system comprises at least one selected from the group consisting of $NR^4$, $NOR^4$, and $N^+R^4R^5$ $An^-$ and the saturated heterocyclic $C_2$-$C_{20}$ring system is optionally substituted with E;

$R^4$ is H or $C_1$-$C_4$alkyl, wherein an alkyl group of the $C_1$-$C_4$alkyl is optionally substituted with D;

$R^5$ is H, $C_1$-$C_4$alkyl, $C_7$-$C_{10}$aralkyl, or $C_3$-$C_5$alkenyl;

$R^6$, $R^7$, $R^8$, $R^9$, and $R^{10}$ are each independently H, $C_1$-$C_{18}$alkyl, $C_3$-$C_{18}$alkenyl, $C_5$-$C_{12}$cycloalkyl, $C_6$-$C_{18}$aryl, or $C_7$-$C_{18}$aralkyl, wherein an alkyl group of the $C_1$-$C_{18}$alkyl, an alkenyl group of the $C_3$-$C_{18}$alkenyl, or a cycloalkyl group of the $C_5$-$C_{12}$cycloalkyl is optionally substituted with D, an aryl group of the $C_6$-$C_{18}$aryl or the $C_7$-$C_{18}$aralkyl is optionally substituted with E;

E is $C_1$-$C_4$alkyl, $C_1$-$C_4$alkoxy, COOH, OH, halogen, $NR^9R^{10}$, —$N^+R^9R^{10}R^5$ $An^-$, $SO_3R^9$, $SO_2NR^9R^{10}$, or $SO_3^-Cat^+$;

D is $C_1$-$C_4$alkoxy, OH, COOH, or halogen;

$An^-$ is an equivalent of an anion; and $Cat^+$ is an equivalent of a cation.

12. A colored composition, comprising:

a high molecular weight organic material, and from 0.01 to 70% by weight, based on a weight of the high molecular weight organic material, of the pigment composition of claim 1.

13. The colored composition of claim 12, wherein the colored composition is a coating composition and the high molecular weight organic material is an organic film-forming binder.

14. A coating prepared by a method comprising curing the coating composition of the colored composition of claim 13 on a substrate.

15. A pigmenting plastic, a coating composition or a printing ink, comprising:

the pigment composition of claim 1.

* * * * *